(12) United States Patent
Miller et al.

(10) Patent No.: US 9,908,876 B2
(45) Date of Patent: *Mar. 6, 2018

(54) IMIDAZO [1,2-A]PYRIDINE COMPOUNDS, SYNTHESIS THEREOF, AND METHODS OF USING SAME

(71) Applicant: UNIVERSITY OF NOTRE DAME DU LAC, Notre Dame, IN (US)

(72) Inventors: Marvin J. Miller, South Bend, IN (US); Garrett C. Moraski, South Bend, IN (US); Lowell D. Markley, South Bend, IN (US); George E. Davis, Carmel, IN (US)

(73) Assignee: UNIVERSITY OF NOTRE DAME DU LAC, Notre Dame, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/056,630

(22) Filed: Feb. 29, 2016

(65) Prior Publication Data

US 2016/0318925 A1 Nov. 3, 2016

Related U.S. Application Data

(63) Continuation of application No. 13/508,011, filed as application No. PCT/US2010/055728 on Nov. 5, 2010, now Pat. No. 9,309,238.

(60) Provisional application No. 61/258,549, filed on Nov. 5, 2009.

(51) Int. Cl.
| C07D 487/04 | (2006.01) |
| C07D 471/04 | (2006.01) |
| A61K 31/437 | (2006.01) |
| A61P 31/06 | (2006.01) |
| A01N 43/90 | (2006.01) |
| A61K 45/06 | (2006.01) |

(52) U.S. Cl.
CPC ........... *C07D 471/04* (2013.01); *A01N 43/90* (2013.01); *A61K 31/437* (2013.01); *A61K 45/06* (2013.01); *C07D 487/04* (2013.01)

(58) Field of Classification Search
CPC .. C07D 487/04; C07D 471/04; A61K 31/437; A61K 31/4355
USPC .......................................... 546/121; 514/300
See application file for complete search history.

(56) References Cited

U.S. PATENT DOCUMENTS

| 4,492,695 A | 1/1985 | Kaplan |
| 4,891,371 A | 1/1990 | George |
| 5,464,843 A | 11/1995 | Hansen, Jr. |
| 5,721,273 A | 2/1998 | Sallee |
| 6,080,767 A | 6/2000 | Klein |
| 6,323,227 B1 | 11/2001 | Klein |
| 6,379,649 B1 | 4/2002 | Katsifis et al. |
| 6,403,588 B1 | 6/2002 | Hayakawa |
| 6,552,037 B2 | 4/2003 | Cai |
| 7,345,055 B2 | 3/2008 | Oberboersch |
| 7,566,781 B2 | 7/2009 | Sakuraba |
| 8,198,449 B2 * | 6/2012 | Pracitto ................ C07D 209/42 546/121 |
| 8,293,909 B2 | 10/2012 | Pracitto |
| 9,309,238 B2 * | 4/2016 | Miller ................... A01N 43/90 |
| 2002/0091116 A1 | 7/2002 | Zhu |
| 2005/0137395 A1 | 6/2005 | Hong |
| 2006/0084806 A1 | 4/2006 | Sridharan |
| 2008/0200473 A1 | 8/2008 | Falco |
| 2009/0163545 A1 | 6/2009 | Goldfarb |
| 2010/0298314 A1 * | 11/2010 | Reddy .................. C07D 487/04 514/233.2 |
| 2011/0166146 A1 | 7/2011 | Fang |
| 2012/0010188 A1 | 1/2012 | Nilsson |

FOREIGN PATENT DOCUMENTS

| DE | 4023215 | 1/1992 |
| EP | 450566 | 10/1991 |
| EP | 499995 | 8/1992 |
| GB | 2006067444 | 6/2006 |
| JP | 05039205 | 2/1993 |
| JP | 09249666 | 9/1997 |
| WO | 1995028389 | 10/1995 |
| WO | 1996002542 | 2/1996 |
| WO | 1999000356 | 1/1999 |
| WO | 1999063940 | 12/1999 |
| WO | 2000078726 | 12/2000 |
| WO | 2001019798 | 3/2001 |
| WO | 2001083481 | 11/2001 |
| WO | 2002020484 | 3/2002 |
| WO | 2004100868 | 11/2004 |
| WO | 2006015737 | 2/2006 |
| WO | 2007015866 | 2/2007 |

(Continued)

OTHER PUBLICATIONS

Mowbray, "Molecules" 2014, 19, 13161-1317.

(Continued)

*Primary Examiner* — Venkataraman Balasubramanian
(74) *Attorney, Agent, or Firm* — Neifeld IP Law, P.C.

(57) ABSTRACT

Embodiments relate to the field of chemistry and biochemistry, and, more specifically, to imidazopyridine compounds, synthesis thereof, and methods of using same. Disclosed herein are various imidazo[1,2-a]pyhdine compounds and methods of using the novel compounds to treat or prevent tuberculosis in a subject or to inhibit fungal growth on plant species. Other embodiments include methods of synthesizing imidazo[1,2-a]pyridine compounds, such as the disclosed imidazo[1,2-a]pyridine compounds.

19 Claims, 58 Drawing Sheets

(56) References Cited

FOREIGN PATENT DOCUMENTS

| WO | 2007136607 | 11/2007 |
|---|---|---|
| WO | 2008038251 | 4/2008 |
| WO | 2008063287 | 5/2008 |
| WO | 2008082490 | 7/2008 |
| WO | 2008109180 | 9/2008 |
| WO | 2008125594 | 10/2008 |
| WO | 2008154271 | 12/2008 |
| WO | 2008109179 | 9/2009 |
| WO | 2009148961 | 12/2009 |
| WO | 2010019796 | 2/2010 |
| WO | 2010030538 | 3/2010 |
| WO | PCT/US10/55728 | 11/2010 |
| WO | 2011050245 | 4/2011 |
| WO | 2011113606 | 9/2011 |

OTHER PUBLICATIONS

2014, Eoh, H., "Tuberculosis xxx" 1-6.
Bosch, "Annu. Rev Phytopathol."., 2014, 52: 175-95.
Anaflous, A., "Armed Imidazo [1,2-a] Pyrimidines (Pyridines): Evaluation of Antibacterial Activity," Letters in Drug Design & Discovery 2004, vol. 1, pp. 224-229.
Kasimogullari, "Fused Heterocycles: Synthesis of Some New Imidazo [1,2-a]-pyridine Derivatives." Molecules, 2004, vol. 9 pp. 894-901.
Kasimogullari, "Fused Heterocycles: Synthesis of Some New Imidazopyridine Derivatives as Anti-Mycobacterial Agents," Turk J. Chem., 2007, vol. 31, pp. 617-622.
Cesur, "Synthesis and Biological Evaluation of Some New Imidazo[1,2-a]pyridines," Acta Chim. Slov., 2010, vol. 57, pp. 355-362.
Odell, "Functionalized 3-amino-imidazo[1,2-a]pyridines: A novel class of drug-like *Mycobacterium tuberculosis* glutamine synthetase inhibitors," Bioorg. Med. Chem. Lett., Jun. 14, 2009, vol. 19, pp. 4790-4793.
Kasimogullari, et al.,"Fused Heterocycles: Synthesis of Some New Imidazo [1,2-a]-pyridine Derivatives." Molecules, 2004, vol. 9, pp. 894-901.
Kasimogullari, et al.,"Fused Heterocycles: Synthesis of Some New Imidazopyridines as Anti-Mycobacterial Agents," Turk J. Chem, 2007, vol. 31, pp. 617-622.
Mowbray, et. al.,"Molecules" 2014, 19 pp. 13161-13176.
Bosch, et al., "Annu. Rev. Phytopathol", 2014. 52: 175-98.
Jul. 20, 2011, International Search Report issued in Application PCT/US2010/055728.
May 8, 2012, International Preliminary Report on Patentability issued in application PCT/US2010/055728.
Jul. 19, 2011, Written Opinion issued in application PCT/US2010/055728.
U.S. Appl. No. 13/508,011.
U.S. Appl. No. 15/056,630.
U.S. Appl. No. 61/258,549, filed Nov. 5, 2009.
U.S. Appl. No. 13/508,011, filed May 3, 2012.
PCT/US10/55728, filed Nov. 5, 2010.
U.S. Appl. No. 15/056,630, filed Feb. 29, 2016.
Odell, Luke R., "Functionalized 3-amino-imidazo[1,2-a]pyridines: A Novel Class of Drug-like Mycobacterium Tuberculosis Glutamine Synthetase Inhibitors,"Bioorganic & Medicinal Chemistry Letters, 2009, vol. 19, pp. 4790-4793.
Anaflous, A., et al., "Armed Imidazo [1,2-a} Pyridines): Evluation of Antibacterial Activity," Letters in Drug Design & Discovery 2004, vol. 1, pp. 224-229.
Kasimogullari, et al., "Fused Heterocycles: Synthesis of Some New Imidazo [1,2-a]-pyridine Derivatives." Molecules, 2004, vol. 9, pp. 894-901.
Kasimogullari, et al., "Fused Heterocycles: Synthesis of Some New Imidazopyridines as Anti-Mycobacterial Agents," Turk J. Chem, 2007, vol. 31, pp. 617-622.
Search Results from Chemical Abstracts, Nov. 12, 2008.
Mowbray, et. al., "Molecules" 2014, 19 pgs. 13161-13176.
Eoh, H., Tuberculosis xxx:, 2014 pp. 1-6.
Bosch, et. al., "Annu. Rev. Phytopathol", 2014. 52: 175-98.
Cesur, "Synthesis and Biological Evaluation of Some New Imidazo[1,2-a]pyridines," Acta Chim. Slov., 2010 vol. 57, pp. 355-362.
International Search Report issued in Application PCT/US2010/055728, dated Jul. 20, 2011.
International Preliminary Report on Patentability issued in application PCT/U82010/055728, dated May 8, 2012.
Written Opinion issued in application PCT/US2010/055728, dated Jul. 19, 2011.
Qiao, L. et al.: "Structure-activity relationship study of EphB3 receptor tyrosine Kinase inhibitors", Bioorganic & Medicinal Chemistry Letters, Pergamon, Amsterdam, NL vol. 19, No. 21 Nov. 1, 2009.
Moraski, Garrett et. al.,: "Preparation and Evaluation of Potent Pentafluorosulfanyl-Substituted Anti-Tuberculosis Compounds", CHEMMEDCHEM, vol. 12, No. 14, Jun. 27, 2017.
Extended European Search Report issued for EP17168780 Completed Sep. 13, 2017, dated Oct. 10, 2017.

* cited by examiner

FIG. 2A

Activity Rankings:

A = ≤2μM   B = <2μM – 10μM   C = <10 μM – 20μM   D = <20 μM – 32μM   E = ≤32 μM

| Compound ID | Mol Wt | GAS: H37Rv TB: MIC 90 | GAST: H37Rv TB: MIC 90 | 7H12: H37Rv TB: MIC 90 | VERO Cells: IC50 |
|---|---|---|---|---|---|
| ND-8462 | 299.75 |  | A | A | E |
| ND-9584 | 322.4 |  | A | A | E |
| ND-9557 | 280.32 |  | A | A | E |
| ND-9560 | 293.36 |  | A | A | E |
| ND-9653 | 439.43 |  | A | A | B |
| ND-9561 | 309.36 |  | A | A | E |
| ND-9585 | 324.33 |  | A | A | E |
| ND-9621 | 333.31 |  | A | A | E |
| ND-9500 | 299.75 |  | A | A | E |
| ND-9628 | 307.35 |  | A | A | E |
| ND-9617 | 283.3 |  | A | A | E |
| ND-9758 | 389.42 |  | A | A | E |
| ND-9873 | 363.33 |  | A | A | E |
| ND-9525 | 309.36 |  | A | A | E |
| ND-9769 | 311.35 |  | A | A | E |
| ND-9761 | 329.78 |  | A | B | E |
| ND-9872 | 337.42 |  | A | A | E |
| ND-9760 | 317.75 |  | A | A | E |
| ND-9903 | 425.4 |  | A | A | E |
| ND-9527 | 313.78 |  | B | A | E |
| ND-9729 | 363.33 |  | A | A | E |
| ND-9759 | 405.88 |  | A | A | B |
| ND-9770 | 323.39 |  | A | A | E |
| ND-9731 | 348.23 |  | A | A | E |
| ND-9727 | 310.35 |  | A | A | E |
| ND-9739 | 309.36 |  | A | A | E |
| ND-9726 | 298.31 |  | A | A | E |
| ND-9734 | 315.32 |  | A | A | E |
| ND-9965 | 357.43 |  | A | B | E |
| ND-9728 | 347.33 |  | A | A | E |
| ND-9620 | 337.27 |  | A | B | D |
| ND-9611 | 420.28 |  | A | A | E |

FIG. 2B

| Compound ID | Mol Wt | GAS: H37Rv TB: MIC 90 | GAST: H37Rv TB: MIC 90 | 7H12: H37Rv TB: MIC 90 | VERO Cells: IC50 |
|---|---|---|---|---|---|
| ND-9740 | 315.32 | | A | A | E |
| ND-9906 | 323.39 | | A | A | E |
| ND-9361 | 297.33 | A | A | B | E |
| ND-9902 | 382.77 | | A | B | E |
| ND-9378 | 279.34 | A | A | B | E |
| ND-9543 | 294.35 | A | A | | E |
| ND-9542 | 314.77 | B | A | | E |
| ND-8668 | 309.36 | A | A | B | E |
| ND-8650 | 313.78 | A | A | B | E |
| ND-9768 | 293.36 | | A | A | E |
| ND-9905 | 337.37 | | A | B | E |
| ND-9654 | 453.46 | | A | A | B |
| ND-9738 | 297.33 | | A | A | E |
| ND-9655 | 425.4 | | A | B | E |
| ND-9635 | 452.51 | | A | B | B |
| ND-9766 | 313.33 | | A | B | E |
| ND-9900 | 337.42 | | A | C | C |
| ND-8654 | 293.36 | | A | A | E |
| ND-9767 | 325.36 | | B | C | E |
| ND-8667 | 309.36 | | A | A | E |
| ND-9904 | 425.4 | | A | B | E |
| ND-9558 | 313.78 | | A | A | E |
| ND-9362 | 297.33 | A | B | B | E |
| ND-8655 | 313.78 | A | A | | B |
| ND-8656 | 293.36 | B | A | | E |
| ND-8675 | 297.33 | B | B | | B |
| ND-8649 | 313.78 | B | B | | E |
| ND-9440 | 309.36 | B | B | | E |
| ND-8666 | 309.36 | B | B | | E |
| ND-9551 | 314.77 | B | B | | E |
| ND-9550 | 335.18 | B | B | | E |
| ND-8454 | 279.34 | A | B | B | E |
| ND-9530 | 310.35 | B | B | | E |
| ND-9623 | 363.26 | C | B | | |
| ND-9529 | 330.77 | B | B | | E |
| ND-8110 | 280.32 | A | B | | E |
| ND-9427 | 280.32 | D | B | | |

FIG. 2C

| Compound ID | Mol Wt | GAS: H37Rv TB: MIC 90 | GAST: H37Rv TB: MIC 90 | 7H12: H37Rv TB: MIC 90 | VERO Cells: IC50 |
|---|---|---|---|---|---|
| ND-8652 | 293.36 | B | B | | E |
| ND-9586 | 358.41 | | B | E | |
| ND-9615 | 331.77 | | B | C | |
| ND-9534 | 296.32 | B | B | | E |
| ND-9546 | 300.74 | B | B | | E |
| ND-9562 | 308.37 | B | B | | E |
| ND-8451 | 348.32 | B | C | B | D |
| ND-9548 | 349.21 | A | B | | E |
| ND-9528 | 329.78 | B | A | A | E |
| ND-9538 | 368.64 | C | B | | |
| ND-9771 | 375.4 | | B | C | E |
| ND-9901 | 286.35 | | B | E | E |
| ND-9535 | 329.78 | B | B | B | E |
| ND-8109 | 300.74 | B | C | C | B |
| ND-9659 | 265.35 | C | B | | E |
| ND-9536 | 334.2 | B | B | A | E |
| ND-9733 | 463.57 | | B | E | E |
| ND-8450 | 294.35 | C | B | B | |
| ND9610 | 435.75 | | B | E | |
| ND-9428 | 313.78 | B | B | | |
| ND-9616 | 259.28 | | B | E | |
| ND-9612 | 403.18 | | B | E | |
| ND-9662 | 299.67 | | B | B | |
| ND-8103 | 281.31 | B | B | | E |
| ND-9544 | 310.35 | B | B | | |
| ND-8669 | 347.33 | B | B | | E |
| ND-8445 | 308.37 | B | C | B | C |
| ND-9426 | 279.34 | C | B | | |
| ND-8448 | 308.37 | B | B | B | E |
| ND-9431 | 294.35 | B | B | | |
| ND-9559 | 348.23 | B | B | | E |
| ND-9665 | 279.25 | | B | B | |
| ND-8102 | 300.74 | B | B | | |
| ND-9434 | 293.36 | B | B | | E |
| ND-9606 | 381.78 | | C | E | |
| ND-9526 | 325.36 | C | B | B | E |
| ND-9952 | 331.39 | | C | E | C |

FIG. 2D

| Compound ID | Mol Wt | GAS: H37Rv TB: MIC 90 | GAST: H37Rv TB: MIC 90 | 7H12: H37Rv TB: MIC 90 | VERO Cells: IC50 |
|---|---|---|---|---|---|
| ND-8446 | 322.4 | C | B | B | E |
| ND-9755 | 363.46 |  | C | E | E |
| ND-9531 | 326.35 | C | C |  |  |
| ND-8457 | 342.39 | C | C |  |  |
| ND-9439 | 348.23 | C | B |  |  |
| ND-9533 | 365.21 | C | C |  |  |
| ND-9663 | 279.25 |  | C | C |  |
| ND-9732 | 293.32 |  | C | E | E |
| ND-9624 | 275.73 |  | C | E |  |
| ND-9499 | 295.34 | E | C | C | E |
| ND-8515 | 328.36 | D | E |  |  |
| ND-9608 | 436.74 | C |  | C |  |
| ND-9547 | 330.77 | C |  | C |  |
| ND-9609 | 470.29 |  | C | C |  |
| ND-9433 | 308.37 | E | D |  |  |
| ND-8458 | 342.39 | E | D |  |  |
| ND-9532 | 324.37 | D | D |  |  |
| ND-9622 | 363.26 |  | D | E |  |
| ND-9537 | 364.23 | D | D |  |  |
| ND-9432 | 310.35 | E | D |  |  |
| ND-8455 | 410.39 | E | D |  |  |
| ND-9541 | 300.74 | E | D |  |  |
| ND-8449 | 348.32 | E | D |  |  |
| ND-8672 | 296.39 | D | D |  |  |
| ND-8660 | 293.36 | E | D | B |  |
| ND-8017 | 265.31 | D | D |  |  |
| ND-9730 | 285.31 |  | E | E | E |
| ND-8106 | 280.32 | D | E |  |  |
| ND-9430 | 314.77 | B | E |  |  |
| ND-8560 | 294.35 | D | E |  |  |
| ND-8670 | 293.36 | D | E |  |  |
| ND-9619 | 313.25 |  | E | E |  |
| ND-8013 | 280.32 | E | E |  |  |
| ND-9564 | 237.26 | E | E |  |  |
| ND-9625 | 275.73 | E |  | E |  |
| ND-9958 | 438.48 |  | E | E | B |
| ND-9626 | 329.7 |  | E | E |  |

FIG. 2E

| Compound ID | Mol Wt | GAS: H37Rv TB: MIC 90 | GAST: H37Rv TB: MIC 90 | 7H12: H37Rv TB: MIC 90 | VERO Cells: IC50 |
|---|---|---|---|---|---|
| ND-9627 | 329.7 | | E | E | |
| ND-9618 | 385.74 | | E | E | |
| ND-9553 | 280.32 | E | E | | |
| ND-9667 | 309.29 | | E | E | |
| ND-9742 | 328.43 | | E | E | E |
| ND-9953 | 357.41 | | E | E | E |
| ND-9954 | 361.82 | | E | E | E |
| ND-9959 | 466.53 | | E | E | E |
| ND-9539 | 367.4 | E | E | | |
| ND-9549 | 307.39 | E | E | | |
| ND-9540 | 266.29 | E | E | | |
| ND-8444 | 294.35 | E | E | | |
| ND-8639 | 369.46 | E | E | | |
| ND-9441 | 279.34 | E | E | | |
| ND-8107 | 319.4 | E | E | | |
| ND-8108 | 328.37 | E | E | | |
| ND-9436 | 349.21 | D | E | | |
| ND-8463 | 341.41 | E | E | | |
| ND-9630 | 436.74 | E | E | | |
| ND-9563 | 327.81 | E | E | | |
| ND-9656 | 350.76 | E | E | | |
| ND-9575 | 403.18 | E | E | | |
| ND-9658 | 299.67 | | | E | |
| ND-9607 | 436.74 | | E | B | |
| ND-9657 | 336.73 | | E | E | |
| ND-8443 | 295.34 | E | | E | |
| ND-9438 | 295.34 | E | E | | |
| ND-8653 | 229.28 | E | E | | |
| ND-8644 | 189.21 | E | E | | |
| ND-9442 | 308.37 | E | E | | |
| ND-8517 | 204.23 | E | E | | |
| ND-8657 | 257.33 | E | E | | |
| ND-8663 | 295.34 | E | E | | |
| ND-8664 | 295.34 | E | E | | |
| ND-9424 | 295.34 | E | E | | |
| ND-8658 | 355.43 | E | E | | |
| ND-8661 | 293.36 | E | E | | |

FIG. 2F

| Compound ID | Mol Wt | GAS: H37Rv TB: MIC 90 | GAST: H37Rv TB: MIC 90 | 7H12: H37Rv TB: MIC 90 | VERO Cells: IC50 |
|---|---|---|---|---|---|
| ND-8665 | 294.35 | E | E | | |
| ND-8681 | 265.31 | E | E | | |
| ND-8105 | 295.34 | E | E | | |
| ND-8020 | 343.38 | E | E | | |
| ND-8474 | 343.38 | E | E | | |
| ND-8015 | 300.74 | E | E | | |
| ND-8447 | 274.32 | E | E | | |
| ND-8460 | 357.41 | E | E | | |
| ND-8461 | 315.75 | E | E | | |
| ND-8662 | 279.34 | E | E | | |
| ND-8453 | 259.3 | E | E | | |
| ND-8456 | 410.39 | E | E | | |
| ND-8464 | 341.41 | E | E | | |
| ND-9569 | 435.75 | E | E | | |
| ND-9567 | 348.23 | E | E | | |
| ND-8459 | 357.41 | E | E | | |
| ND-9566 | 331.77 | E | E | | |
| ND-9570 | 385.74 | E | E | | |
| ND-9574 | 470.29 | E | E | | |
| ND-9576 | 436.74 | E | E | | |
| ND-8104 | 271.36 | E | E | | |
| ND-9571 | 402.2 | E | E | | |
| ND-9572 | 402.2 | E | E | | |
| ND-9578 | 248.13 | E | E | | |
| ND-9568 | 348.23 | E | E | | |
| ND-9425 | 283.3 | E | E | | |
| ND-9423 | 265.31 | E | E | | |
| ND-9565 | 381.78 | E | E | | |
| ND-9422 | 299.75 | E | E | | |
| ND-9429 | 309.36 | E | E | | |
| ND-9552 | 369.63 | C | E | | |
| ND-9554 | 296.32 | E | E | | |
| ND-9573 | 386.73 | E | E | | |
| ND-9435 | 348.23 | E | E | | |
| ND-9437 | 334.2 | E | E | | |
| ND-9555 | 335.18 | E | E | | |
| ND-10059 | 314.77 | | | B | |

FIG. 2G

| Compound ID | Mol Wt | GAS: H37Rv TB: MIC 90 | GAST: H37Rv TB: MIC 90 | 7H12: H37Rv TB: MIC 90 | VERO Cells: IC50 |
|---|---|---|---|---|---|
| ND-10058 | 371.45 | | | B | |
| ND-10060 | 283.33 | | | A | |
| ND-10053 | 403.45 | | | A | |
| ND-10056 | 323.39 | | | B | |
| ND-10047 | 310.35 | | | B | |
| ND-10024 | 479.37 | | | C | |
| ND-10028 | 307.31 | | | C | |
| ND-10027 | 385.44 | | | C | |
| ND-10021 | 351.3 | | | A | |
| ND-10020 | 363.33 | | | A | |
| ND-10023 | 364.32 | | | C | |
| ND-10022 | 443.39 | | | A | |
| ND-10035 | 489.47 | | | C | |
| ND-10034 | 411.4 | | | C | |
| ND-10046 | 324.37 | | | A | |
| ND-10038 | 327.46 | | | C | |
| ND-10030 | 411.4 | | | B | |
| ND-10029 | 384.47 | | | C | |
| ND-10033 | 351.3 | | | B | |
| ND-10032 | 363.33 | | | B | |
| ND-9650 | 298.31 | | A | A | E |
| ND-9651 | 280.32 | | A | A | E |
| ND-9652 | 310.35 | | A | A | E |
| ND-10054 | 338.4 | | | C | |
| ND-10057 | 358.41 | | | B | |

FIG. 3A

Activity Rankings:
200 ppm. IDP Disease Control Rankings
A: %DC > 50
B: %DC > 25, ≤ 50
C: %DC ≤ 25

| Compound ID | Mol Wt | PUCCRT | SEPTTR |
|---|---|---|---|
| ND-7620 | 299.75 | C | C |
| ND-8013 | 322.4 | B | B |
| ND-8015 | 280.32 | A | A |
| ND-8016 | 293.36 | A | C |
| ND-8017 | 439.43 | C | C |
| ND-8020 | 309.36 | A | B |
| ND-8445 | 324.33 | A | A |
| ND-8447 | 333.31 | C | C |
| ND-8448 | 299.75 | C | C |
| ND-8449 | 307.35 | C | B |
| ND-8450 | 283.3 | A | B |
| ND-8451 | 389.42 | C | A |
| ND-8453 | 363.33 | C | C |
| ND-8454 | 309.36 | C | C |
| ND-8456 | 311.35 | C | C |
| ND-8457 | 329.78 | C | C |
| ND-8458 | 337.42 | C | C |
| ND-8459 | 317.75 | C | C |
| ND-8461 | 425.4 | B | C |
| ND-8462 | 313.78 | C | C |
| ND-8464 | 363.33 | C | C |
| ND-8670 | 323.39 | C | C |
| ND-8656 | 348.23 | B | C |
| ND-8664 | 310.35 | A | C |
| ND-8667 | 309.36 | C | C |
| ND-8662 | 298.31 | A | C |
| ND-8661 | 315.32 | B | C |
| ND-8657 | 347.33 | A | C |
| ND-8652 | 337.27 | B | C |
| ND-8654 | 420.28 | A | C |
| ND-8655 | 315.32 | B | C |
| ND-8660 | 323.39 | A | C |
| ND-8649 | 297.33 | A | C |
| ND-8659 | 382.77 | A | C |
| ND-8663 | 279.34 | A | C |
| ND-8669 | 294.35 | C | C |
| ND-8672 | 314.77 | B | C |
| ND-8651 | 309.36 | A | C |

FIG. 3B

| | | | |
|---|---|---|---|
| ND-8658 | 313.78 | B | C |
| ND-8650 | 293.36 | C | C |
| ND-8653 | 453.46 | C | C |
| ND-8665 | 297.33 | C | C |
| ND-8668 | 425.4 | C | B |
| ND-8644 | 313.33 | C | C |
| ND-9378 | 337.42 | C | C |
| ND-9422 | 293.36 | C | B |
| ND-9423 | 325.36 | C | B |
| ND-9424 | 309.36 | C | C |
| ND-9425 | 425.4 | C | C |
| ND-9426 | 313.78 | C | C |
| ND-9427 | 313.78 | C | A |
| ND-9428 | 293.36 | C | B |
| ND-9429 | 313.78 | C | C |
| ND-9430 | 309.36 | C | B |
| ND-9431 | 314.77 | C | B |
| ND-9432 | 335.18 | A | A |
| ND-9433 | 279.34 | A | A |
| ND-9434 | 310.35 | C | B |
| ND-9436 | 331.39 | C | C |
| ND-9437 | 363.26 | C | B |
| ND-9438 | 330.77 | C | C |
| ND-9439 | 280.32 | C | C |
| ND-9440 | 280.32 | C | C |
| ND-9442 | 293.36 | C | B |
| ND-9499 | 358.41 | C | C |
| ND-9500 | 331.77 | C | A |
| ND-9565 | 296.32 | C | C |
| ND-9566 | 300.74 | A | C |
| ND-9567 | 308.37 | C | C |
| ND-9568 | 348.32 | C | C |
| ND-9574 | 349.21 | C | C |
| ND-9569 | 329.78 | C | C |
| ND-9573 | 368.64 | C | C |
| ND-9570 | 286.35 | C | C |
| ND-9571 | 329.78 | C | C |
| ND-9575 | 300.74 | C | C |
| ND-9576 | 334.2 | C | C |
| ND-9572 | 294.35 | C | C |
| ND-9577 | 435.75 | C | C |
| ND-9578 | 313.78 | C | C |
| ND-9525 | 259.28 | C | B |
| ND-9526 | 403.18 | C | C |
| ND-9527 | 281.31 | C | C |
| ND-9528 | 310.35 | C | A |

FIG. 3C

| | | | |
|---|---|---|---|
| ND-9530 | 347.33 | C | A |
| ND-9531 | 308.37 | C | A |
| ND-9533 | 279.34 | C | A |
| ND-9534 | 308.37 | C | A |
| ND-9535 | 294.35 | C | A |
| ND-9536 | 348.23 | C | B |
| ND-9537 | 293.36 | C | A |
| ND-9538 | 381.78 | C | B |
| ND-9540 | 325.36 | C | C |
| ND-9541 | 363.46 | C | C |
| ND-9542 | 326.33 | C | A |
| ND-9543 | 342.39 | C | A |
| ND-9544 | 348.23 | C | B |
| ND-9546 | 363.21 | C | B |
| ND-9547 | 275.73 | C | A |
| ND-9548 | 295.34 | C | A |
| ND-9550 | 328.36 | C | C |
| ND-9551 | 436.74 | C | A |
| ND-9552 | 330.77 | C | B |
| ND-9553 | 470.29 | C | B |
| ND-9554 | 308.37 | C | C |
| ND-9555 | 342.39 | C | C |
| ND-9557 | 324.37 | B | A |
| ND-9558 | 363.26 | C | A |
| ND-9559 | 364.23 | C | B |
| ND-9560 | 310.35 | C | C |
| ND-9561 | 300.74 | C | A |
| ND-9562 | 348.32 | A | A |
| ND-9563 | 293.36 | C | C |
| ND-9564 | 265.31 | C | C |
| ND-9606 | 280.32 | C | C |
| ND-9607 | 314.77 | C | C |
| ND-9608 | 294.35 | C | C |
| ND-9609 | 293.36 | C | C |
| ND-9610 | 313.25 | C | C |
| ND-9611 | 280.32 | C | C |
| ND-9612 | 227.26 | C | C |
| ND-9985 | 357.43 | C | C |
| ND-10020 | 363.33 | C | C |
| ND-10021 | 351.3 | C | C |
| ND-10022 | 443.39 | C | C |
| ND-10023 | 364.32 | C | C |
| ND-10027 | 385.44 | C | C |
| ND-10028 | 307.31 | C | C |
| ND-10029 | 384.47 | C | C |
| ND-10030 | 411.4 | C | C |

FIG. 3D

| | | | |
|---|---|---|---|
| ND-10031 | 232.28 | C | C |
| ND-10032 | 363.33 | C | C |
| ND-10033 | 351.3 | C | C |
| ND-10034 | 411.4 | C | C |
| ND-10035 | 489.47 | C | C |
| ND-10036 | 364.32 | C | C |
| ND-10037 | 352.29 | C | C |
| ND-10038 | 327.46 | C | C |
| ND-10047 | 310.35 | C | A |
| ND-10056 | 323.39 | C | C |
| ND-10057 | 358.41 | C | C |
| ND-10058 | 371.45 | C | C |
| ND-10059 | 314.77 | C | C |
| ND-10060 | 283.33 | C | C |

FIG. 4A
| Compound ID | Structure | Mol Wt | Formula |
|---|---|---|---|
| ND-6013 | 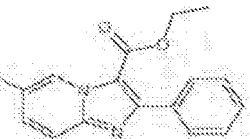 | 280.32 | $C_{17}H_{16}N_2O_2$ |
| ND-6015 | 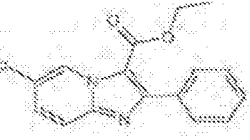 | 300.74 | $C_{16}H_{13}ClN_2O_2$ |
| ND-6017 | 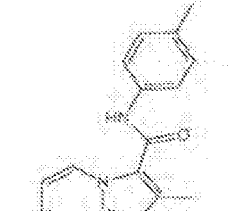 | 265.31 | $C_{17}H_{15}N_3O$ |
| ND-6020 | 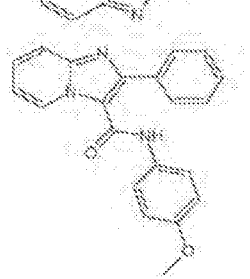 | 343.38 | $C_{22}H_{17}N_3O_2$ |
| ND-6102 | 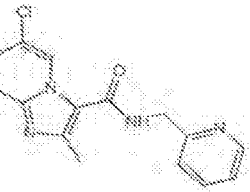 | 300.74 | $C_{18}H_{15}ClN_2O$ |

FIG. 4B

| Compound ID | Structure | Mol Wt | Formula |
|---|---|---|---|
| ND-8103 | 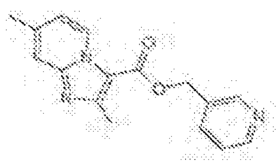 | 281.31 | $C_{16}H_{15}N_3O_2$ |
| ND-8104 | 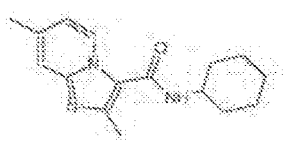 | 271.36 | $C_{17}H_{21}N_3O$ |
| ND-8105 | 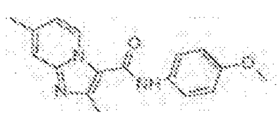 | 295.34 | $C_{17}H_{17}N_3O_2$ |
| ND-8106 | 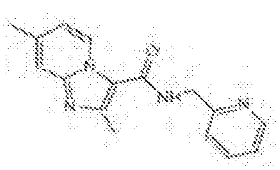 | 280.32 | $C_{16}H_{16}N_4O$ |
| ND-8107 | 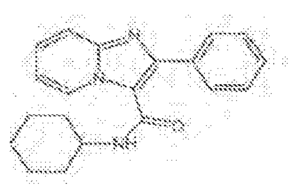 | 319.4 | $C_{20}H_{21}N_3O$ |

FIG. 4C

| Compound ID | Structure | Mol Wt | Formula |
|---|---|---|---|
| ND-8108 | | 328.37 | $C_{21}H_{17}N_3O$ |
| ND-8109 | 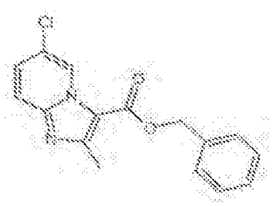 | 300.74 | $C_{16}H_{13}ClN_2O_2$ |
| ND-8110 | 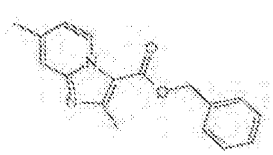 | 280.32 | $C_{17}H_{16}N_2O_2$ |
| ND-8443 | 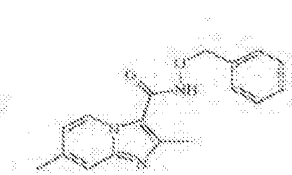 | 295.34 | $C_{17}H_{17}N_3O_2$ |
| ND-8444 | 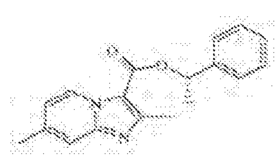 | 294.35 | $C_{18}H_{18}N_2O_2$ |

FIG. 4D

| Compound ID | Structure | Mol Wt | Formula |
|---|---|---|---|
| ND-8445 | 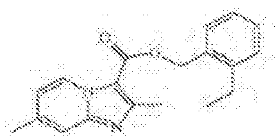 | 308.37 | $C_{19}H_{20}N_2O_2$ |
| ND-8446 | 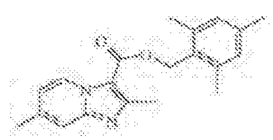 | 322.4 | $C_{20}H_{22}N_2O_2$ |
| ND-8447 | 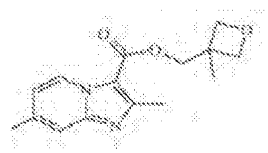 | 274.32 | $C_{16}H_{18}N_2O_2$ |
| ND-8448 | 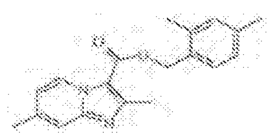 | 308.37 | $C_{19}H_{20}N_2O_2$ |
| ND-8449 | 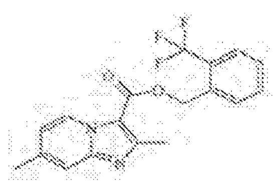 | 348.32 | $C_{19}H_{16}F_3N_2O_2$ |

FIG. 4E

| Compound ID | Structure | Mol Wt | Formula |
|---|---|---|---|
| ND-8450 | 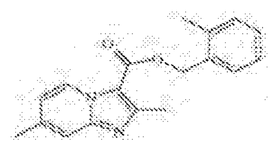 | 294.35 | $C_{19}H_{18}N_2O_2$ |
| ND-8451 | 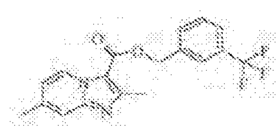 | 348.32 | $C_{19}H_{15}F_3N_2O_2$ |
| ND-8453 | 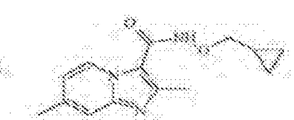 | 258.3 | $C_{15}H_{18}N_2O_2$ |
| ND-8454 | 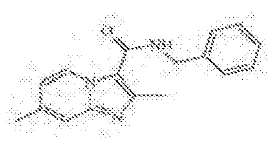 | 279.34 | $C_{18}H_{17}N_3O$ |
| ND-8455 | 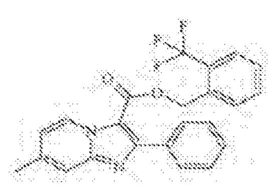 | 410.39 | $C_{23}H_{17}F_3N_2O_2$ |

FIG. 4F

| Compound ID | Structure | Mol Wt | Formula |
|---|---|---|---|
| ND-8456 | 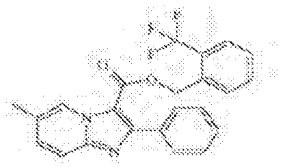 | 410.39 | $C_{25}H_{19}F_2N_2O_2$ |
| ND-8457 | 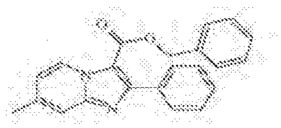 | 342.39 | $C_{23}H_{18}N_2O_2$ |
| ND-8458 | 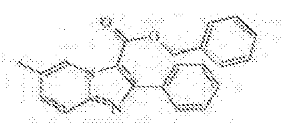 | 342.39 | $C_{23}H_{18}N_2O_2$ |
| ND-8459 | 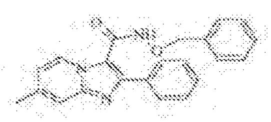 | 357.41 | $C_{23}H_{19}N_3O$ |
| ND-8460 | 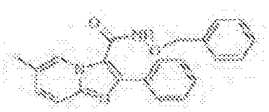 | 357.41 | $C_{23}H_{19}N_3O$ |

FIG. 4G

| Compound ID | Structure | Mol Wt | Formula |
|---|---|---|---|
| ND-8461 | 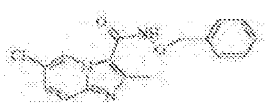 | 315.75 | $C_{18}H_{14}ClN_3O_2$ |
| ND-8462 | 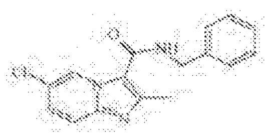 | 299.75 | $C_{18}H_{14}ClN_3O$ |
| ND-8463 | 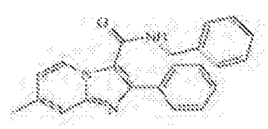 | 341.41 | $C_{23}H_{19}N_3O$ |
| ND-8464 | 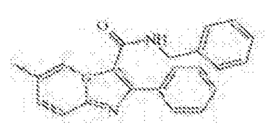 | 341.41 | $C_{23}H_{19}N_3O$ |
| ND-8474 | 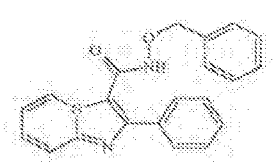 | 343.38 | $C_{21}H_{17}N_3O_2$ |

FIG. 4H

| Compound ID | Structure | Mol Wt | Formula |
|---|---|---|---|
| ND-8515 | 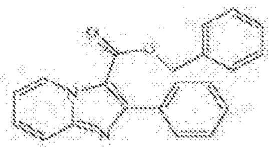 | 328.36 | $C_{22}H_{16}N_2O_2$ |
| ND-8517 | 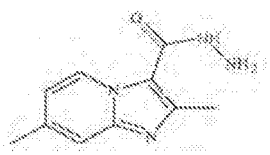 | 204.23 | $C_{12}H_{12}N_2O$ |
| ND-8560 | 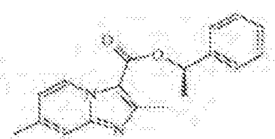 | 294.35 | $C_{19}H_{18}N_2O_2$ |
| ND-8644 | 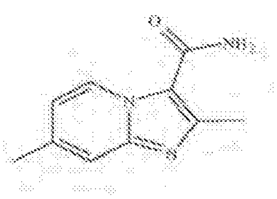 | 189.21 | $C_{11}H_{11}N_2O$ |
| ND-8649 | 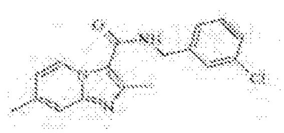 | 313.78 | $C_{18}H_{16}ClN_2O$ |

FIG. 4I

| Compound ID | Structure | Mol Wt | Formula |
|---|---|---|---|
| ND-8650 | 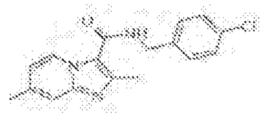 | 313.78 | $C_{17}H_{15}ClN_2O$ |
| ND-8651 | 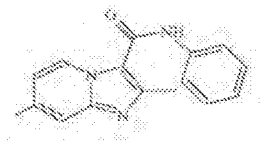 | 285.31 | $C_{18}H_{15}N_3O$ |
| ND-8652 | 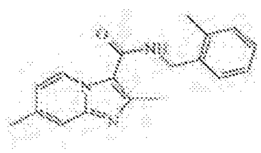 | 293.36 | $C_{19}H_{19}N_2O$ |
| ND-8653 | 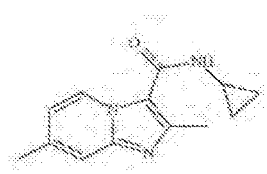 | 229.28 | $C_{13}H_{13}N_2O$ |
| ND-8654 | 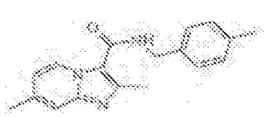 | 293.36 | $C_{19}H_{19}N_2O$ |

FIG. 4J

| Compound ID | Structure | Mol Wt | Formula |
|---|---|---|---|
| ND-8655 | 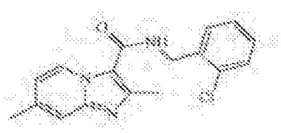 | 313.78 | C₁₇H₁₆ClN₃O |
| ND-8656 | 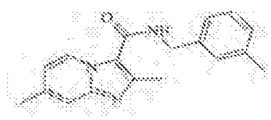 | 293.36 | C₁₈H₁₉N₃O |
| ND-8657 | 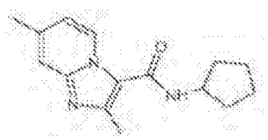 | 257.33 | C₁₅H₁₉N₃O |
| ND-8658 | 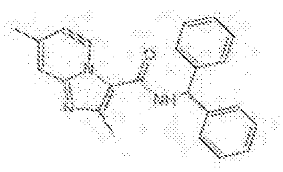 | 355.43 | C₂₃H₂₁N₃O |
| ND-8659 | 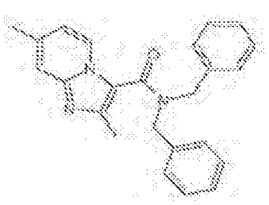 | 369.46 | C₂₄H₂₃N₃O |

FIG. 4K

| Compound ID | Structure | Mol Wt | Formula |
|---|---|---|---|
| ND-8660 | 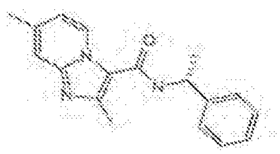 | 293.36 | $C_{18}H_{19}N_3O$ |
| ND-8661 | 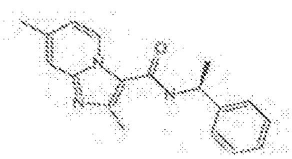 | 293.36 | $C_{18}H_{19}N_3O$ |
| ND-8662 | 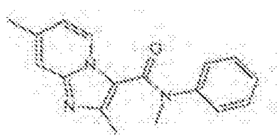 | 279.34 | $C_{17}H_{17}N_3O$ |
| ND-8663 | 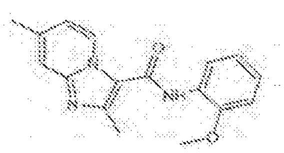 | 295.34 | $C_{17}H_{17}N_3O_2$ |
| ND-8664 | 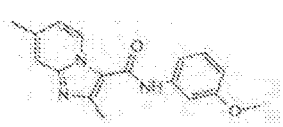 | 295.34 | $C_{17}H_{17}N_3O_2$ |

FIG. 4L

| Compound ID | Structure | Mol Wt | Formula |
|---|---|---|---|
| ND-8665 | 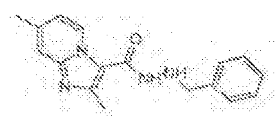 | 294.35 | $C_{19}H_{18}N_2O$ |
| ND-8666 | 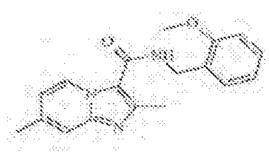 | 309.36 | $C_{19}H_{19}N_2O_2$ |
| ND-8667 | 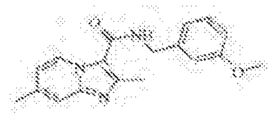 | 309.36 | $C_{19}H_{19}N_2O_2$ |
| ND-8668 | 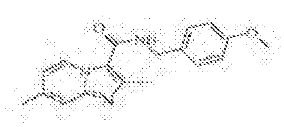 | 309.36 | $C_{19}H_{19}N_2O_2$ |
| ND-8669 | 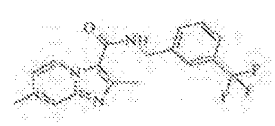 | 347.33 | $C_{19}H_{16}F_3N_2O$ |

FIG. 4M

| Compound ID | Structure | Mol Wt | Formula |
|---|---|---|---|
| ND-8670 | 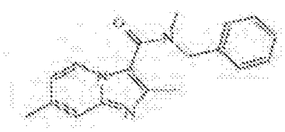 | 293.36 | $C_{18}H_{19}N_3O$ |
| ND-8672 | 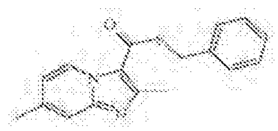 | 298.39 | $C_{17}H_{18}N_2OS$ |
| ND-8675 | 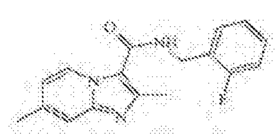 | 297.33 | $C_{17}H_{16}FN_3O$ |
| ND-9361 | 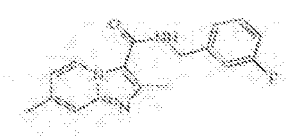 | 297.33 | $C_{17}H_{16}FN_3O$ |
| ND-9362 | 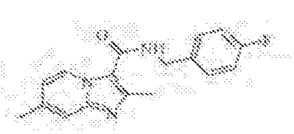 | 297.33 | $C_{17}H_{16}FN_3O$ |

FIG. 4N
| Compound ID | Structure | Mol Wt | Formula |
|---|---|---|---|
| ND-9378 | 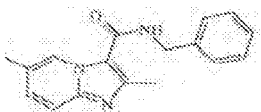 | 279.34 | $C_{17}H_{17}N_3O$ |
| ND-9422 | 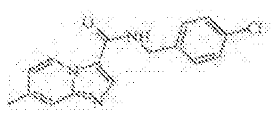 | 299.75 | $C_{16}H_{14}ClN_3O$ |
| ND-9423 | 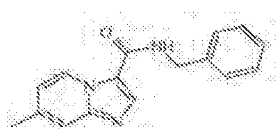 | 265.31 | $C_{16}H_{15}N_3O$ |
| ND-9424 | 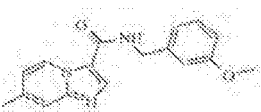 | 295.34 | $C_{17}H_{17}N_3O_2$ |
| ND-9425 | 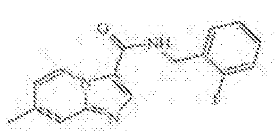 | 283.3 | $C_{16}H_{14}FN_3O$ |

FIG. 4O

| Compound ID | Structure | Mol Wt | Formula |
|---|---|---|---|
| ND-9426 | 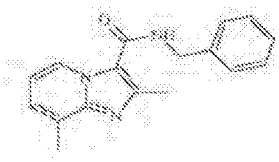 | 279.34 | C₁₇H₁₇N₃O |
| ND-9427 | 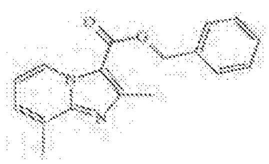 | 280.32 | C₁₇H₁₆N₂O₂ |
| ND-9428 | 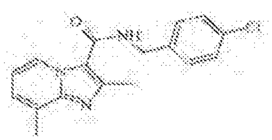 | 313.78 | C₁₇H₁₆ClN₃O |
| ND-9429 | 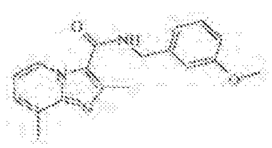 | 309.36 | C₁₈H₁₉N₃O₂ |
| ND-9430 | 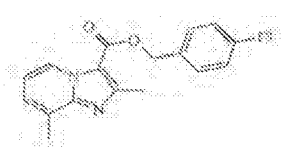 | 314.77 | C₁₇H₁₅ClN₂O₂ |

FIG. 4P

| Compound ID | Structure | Mol Wt | Formula |
|---|---|---|---|
| ND-9431 | 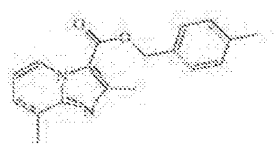 | 294.35 | $C_{18}H_{18}N_2O_2$ |
| ND-9432 | 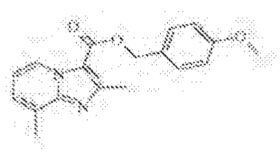 | 310.35 | $C_{18}H_{18}N_2O_3$ |
| ND-9433 | 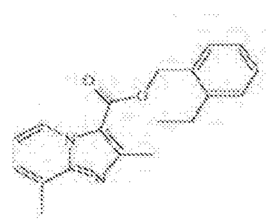 | 308.37 | $C_{19}H_{20}N_2O_2$ |
| ND-9434 | 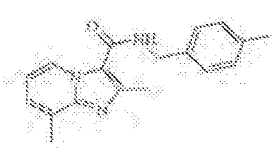 | 293.36 | $C_{18}H_{19}N_3O$ |
| ND-9435 | 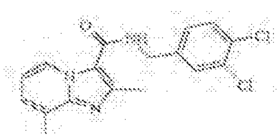 | 348.23 | $C_{17}H_{13}Cl_2N_3O$ |

FIG. 4Q

| Compound ID | Structure | Mol Wt | Formula |
|---|---|---|---|
| ND-9436 | 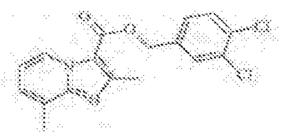 | 349.21 | C$_{17}$H$_{15}$Cl$_2$N$_2$O$_2$ |
| ND-9437 | 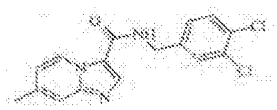 | 334.2 | C$_{17}$H$_{13}$Cl$_2$N$_3$O |
| ND-9438 | 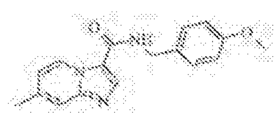 | 295.34 | C$_{17}$H$_{17}$N$_3$O$_2$ |
| ND-9439 | 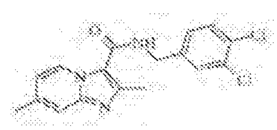 | 348.23 | C$_{17}$H$_{14}$Cl$_2$N$_4$O |
| ND-9440 | 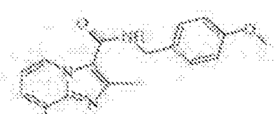 | 309.36 | C$_{17}$H$_{19}$N$_3$O$_2$ |

FIG. 4R
| Compound ID | Structure | Mol Wt | Formula |
|---|---|---|---|
| ND-9441 | 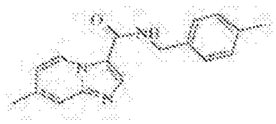 | 279.34 | $C_{17}H_{17}N_3O$ |
| ND-9442 | 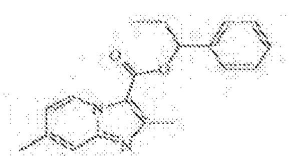 | 308.37 | $C_{19}H_{20}N_2O_2$ |
| ND-9499 | 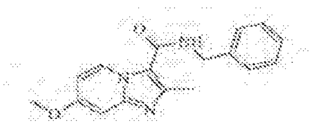 | 295.34 | $C_{18}H_{17}N_2O_2$ |
| ND-9500 | 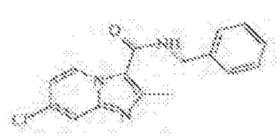 | 299.75 | $C_{17}H_{14}ClN_2O$ |
| ND-9525 | 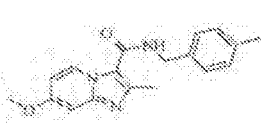 | 309.38 | $C_{19}H_{19}N_2O_2$ |

FIG. 4S

| Compound ID | Structure | Mol Wt | Formula |
|---|---|---|---|
| ND-9526 | 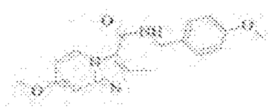 | 325.36 | $C_{19}H_{19}N_3O_3$ |
| ND-9527 | 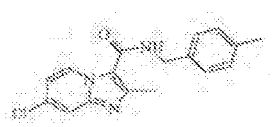 | 313.78 | $C_{17}H_{16}ClN_3O$ |
| ND-9528 | 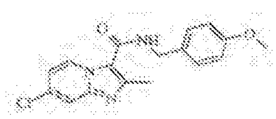 | 329.78 | $C_{17}H_{16}ClN_3O_2$ |
| ND-9529 | 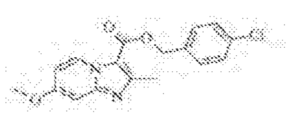 | 330.77 | $C_{17}H_{15}ClN_2O_3$ |
| ND-9530 | 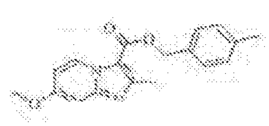 | 310.35 | $C_{18}H_{18}N_2O_3$ |

FIG. 4T

| Compound ID | Structure | Mol Wt | Formula |
|---|---|---|---|
| ND-9531 | 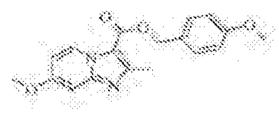 | 326.35 | $C_{19}H_{18}N_2O_3$ |
| ND-9532 | 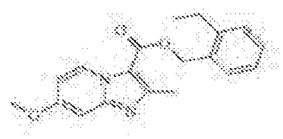 | 324.37 | $C_{20}H_{20}N_2O_2$ |
| ND-9533 | 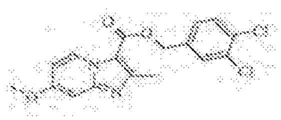 | 365.21 | $C_{17}H_{12}Cl_2N_2O_3$ |
| ND-9534 | 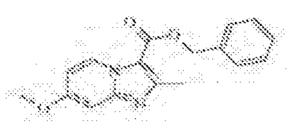 | 296.32 | $C_{17}H_{16}N_2O_3$ |
| ND-9535 | 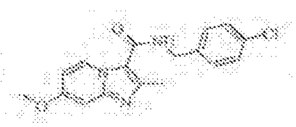 | 330.78 | $C_{17}H_{15}ClN_2O_3$ |

FIG. 4U
| Compound ID | Structure | Mol Wt | Formula |
|---|---|---|---|
| ND-9536 | 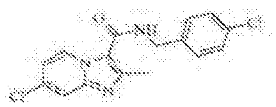 | 334.2 | $C_{16}H_{12}Cl_2N_2O$ |
| ND-9537 | 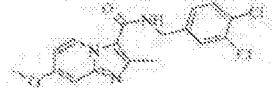 | 364.23 | $C_{17}H_{14}Cl_2N_2O_2$ |
| ND-9538 | 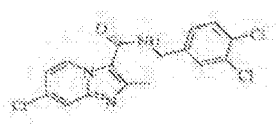 | 368.04 | $C_{16}H_{11}Cl_3N_2O$ |
| ND-9539 | 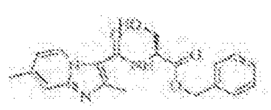 | 387.4 | $C_{23}H_{17}N_3O_3$ |
| ND-9540 | 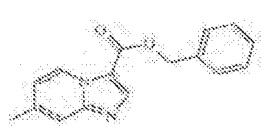 | 266.29 | $C_{16}H_{14}N_2O_2$ |

FIG. 4V

| Compound ID | Structure | Mol Wt | Formula |
|---|---|---|---|
| ND-9541 | 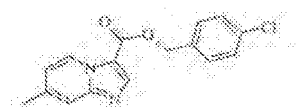 | 300.74 | $C_{16}H_{13}ClN_2O_2$ |
| ND-9542 | 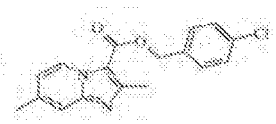 | 314.77 | $C_{17}H_{15}ClN_2O_2$ |
| ND-9543 | 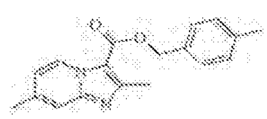 | 294.35 | $C_{18}H_{18}N_2O_2$ |
| ND-9544 | 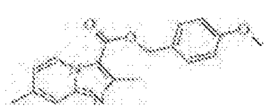 | 310.35 | $C_{18}H_{18}N_2O_3$ |
| ND-9546 | 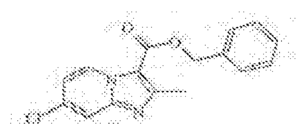 | 300.74 | $C_{16}H_{13}ClN_2O_2$ |

FIG. 4W
| Compound ID | Structure | Mol Wt | Formula |
|---|---|---|---|
| ND-9547 | 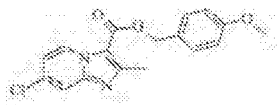 | 330.77 | $C_{17}H_{15}ClN_2O_3$ |
| ND-9548 | 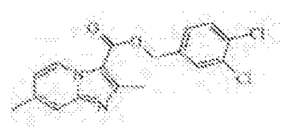 | 349.21 | $C_{17}H_{14}Cl_2N_2O_2$ |
| ND-9550 | 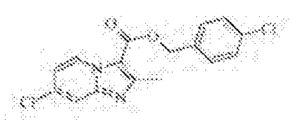 | 335.18 | $C_{16}H_{12}Cl_2N_2O_2$ |
| ND-9551 | 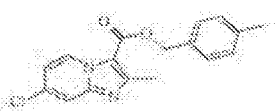 | 314.77 | $C_{17}H_{15}ClN_2O_2$ |
| ND-9552 | 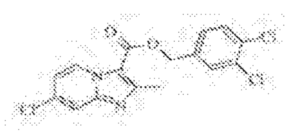 | 369.63 | $C_{16}H_{11}ClBrN_2O_2$ |

FIG. 4X

| Compound ID | Structure | Mol Wt | Formula |
|---|---|---|---|
| ND-9553 | 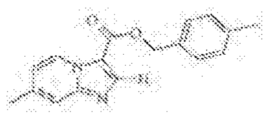 | 280.32 | $C_{17}H_{16}N_2O_2$ |
| ND-9554 | 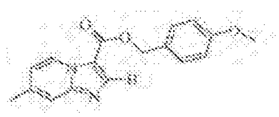 | 296.32 | $C_{17}H_{16}N_2O_3$ |
| ND-9556 | 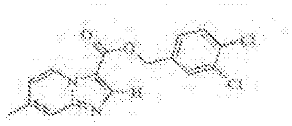 | 335.18 | $C_{16}H_{12}ClN_2O_2$ |
| ND-9557 | 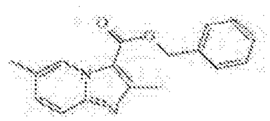 | 280.32 | $C_{17}H_{16}N_2O_2$ |
| ND-9558 | 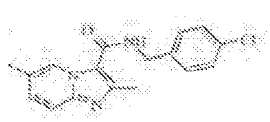 | 313.78 | $C_{17}H_{15}ClN_2O$ |

FIG. 4Y
| Compound ID | Structure | Mol Wt | Formula |
|---|---|---|---|
| ND-9559 | 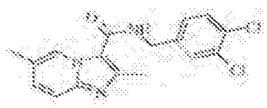 | 348.23 | $C_{17}H_{15}Cl_2N_3O$ |
| ND-9560 | 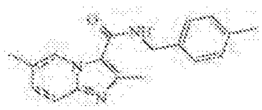 | 293.36 | $C_{18}H_{19}N_3O$ |
| ND-9561 | 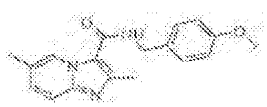 | 309.36 | $C_{18}H_{19}N_3O_2$ |
| ND-9562 | 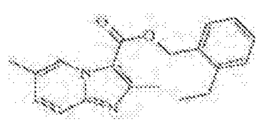 | 308.37 | $C_{19}H_{20}N_2O_2$ |
| ND-9563 | 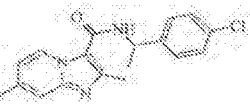 | 327.81 | $C_{18}H_{18}ClN_3O$ |

FIG. 4Z

| Compound ID | Structure | Mol Wt | Formula |
|---|---|---|---|
| ND-9564 | 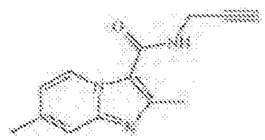 | 227.26 | C₁₃H₁₃N₃O |
| ND-9565 | 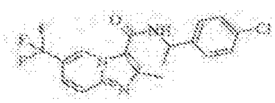 | 381.78 | C₁₈H₁₃ClF₃N₃O |
| ND-9566 | 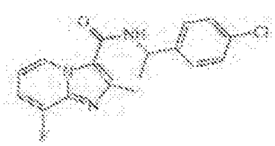 | 331.77 | C₁₇H₁₄ClFN₃O |
| ND-9567 | 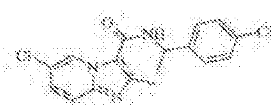 | 348.23 | C₁₇H₁₃Cl₂N₃O |
| ND-9568 | 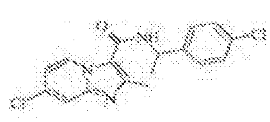 | 348.23 | C₁₇H₁₃Cl₂N₃O |

FIG. 4AA

| Compound ID | Structure | Mol Wt | Formula |
|---|---|---|---|
| ND-9569 | 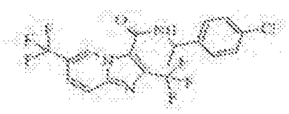 | 435.75 | $C_{19}H_{13}ClF_5N_3O$ |
| ND-9570 | 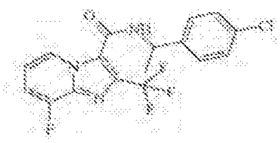 | 386.74 | $C_{17}H_{12}ClF_3N_3O$ |
| ND-9571 | 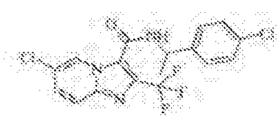 | 402.2 | $C_{17}H_{12}Cl_2F_3N_3O$ |
| ND-9572 | 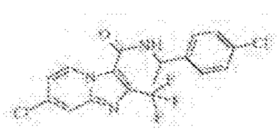 | 402.2 | $C_{17}H_{12}Cl_2F_3N_3O$ |
| ND-9573 | 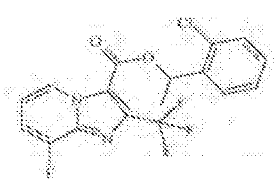 | 386.73 | $C_{17}H_{11}ClF_3N_3O_2$ |

FIG. 4BB

| Compound ID | Structure | Mol Wt | Formula |
|---|---|---|---|
| ND-9574 | 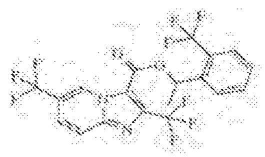 | 470.29 | $C_{19}H_{11}F_7N_2O_2$ |
| ND-9575 | 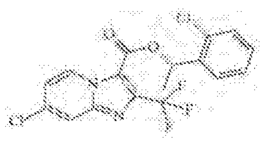 | 403.18 | $C_{19}H_{11}Cl_2F_3N_2O_2$ |
| ND-9576 | 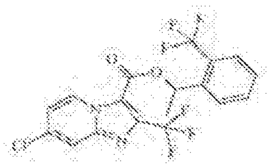 | 436.74 | $C_{19}H_{11}ClF_5N_2O_2$ |
| ND-9578 | 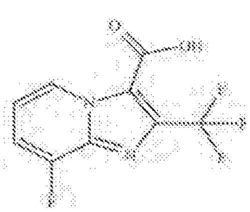 | 248.13 | $C_{12}H_9F_3N_2O_2$ |
| ND-9584 | 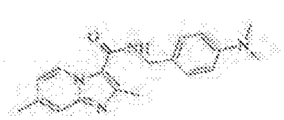 | 322.4 | $C_{19}H_{22}N_4O$ |

FIG. 4CC
| Compound ID | Structure | Mol Wt | Formula |
|---|---|---|---|
| ND-9585 | 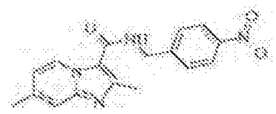 | 324.33 | $C_{17}H_{16}N_2O_3$ |
| ND-9586 | 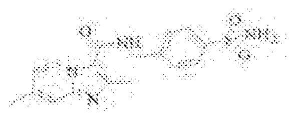 | 358.41 | $C_{17}H_{18}N_2O_3S$ |
| ND-9606 | 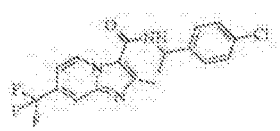 | 381.78 | $C_{19}H_{12}ClF_3N_2O$ |
| ND-9607 | 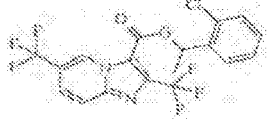 | 436.74 | $C_{19}H_{11}ClF_3N_2O_2$ |
| ND-9608 | 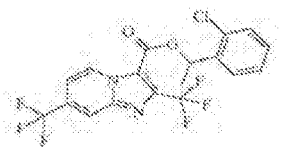 | 436.74 | $C_{19}H_{11}ClF_3N_2O_2$ |

FIG. 4DD

| Compound ID | Structure | Mol Wt | Formula |
|---|---|---|---|
| ND-9609 | 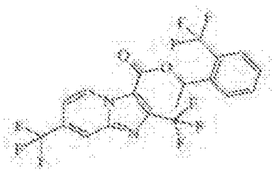 | 470.29 | $C_{19}H_{11}F_9N_2O_2$ |
| ND-9610 | 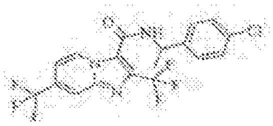 | 435.75 | $C_{18}H_{12}ClF_6N_2O$ |
| ND-9611 | 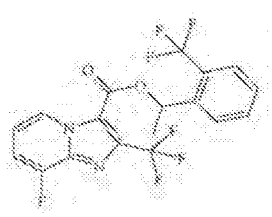 | 420.28 | $C_{19}H_{13}F_7N_2O_2$ |
| ND-9612 | 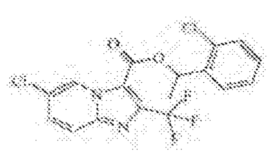 | 403.18 | $C_{17}H_{10}ClF_5N_2O_2$ |
| ND-9615 | 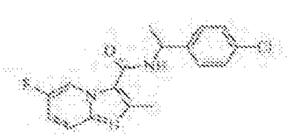 | 331.77 | $C_{17}H_{15}ClFN_3O$ |

FIG. 4EE

| Compound ID | Structure | Mol Wt | Formula |
|---|---|---|---|
| ND-9616 | 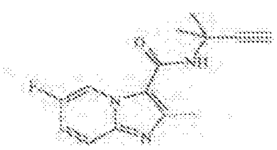 | 259.28 | C₁₄H₁₄FN₃O |
| ND-9617 | 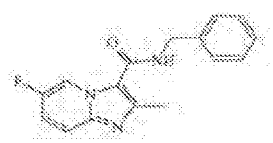 | 283.3 | C₁₆H₁₄FN₃O |
| ND-9618 | 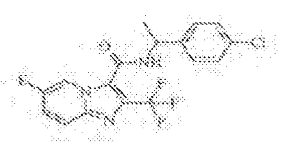 | 365.74 | C₁₇H₁₃ClF₃N₃O |
| ND-9619 | 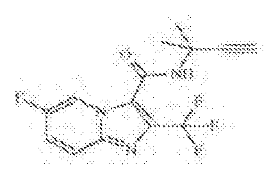 | 313.25 | C₁₅H₁₃F₃N₃O |
| ND-9620 | 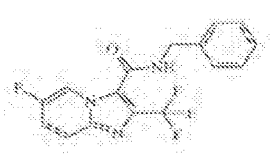 | 337.27 | C₁₇H₁₃F₃N₃O |

FIG. 4FF

| Compound ID | Structure | Mol Wt | Formula |
|---|---|---|---|
| ND-9821 | | 333.31 | C17H14F3N3O |
| ND-9822 | | 363.28 | C18H16F3N3O |
| ND-9823 | | 363.28 | C18H16F3N3O |
| ND-9824 | | 275.73 | C14H14ClN3O |
| ND-9825 | | 275.73 | C14H14ClN3O |

FIG. 4GG

| Compound ID | Structure | Mol Wt | Formula |
|---|---|---|---|
| ND-9626 | | 329.7 | $C_{15}H_{13}ClF_3N_3O$ |
| ND-9627 | 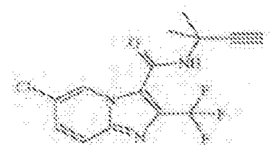 | 329.7 | $C_{15}H_{13}ClF_3N_3O$ |
| ND-9628 | 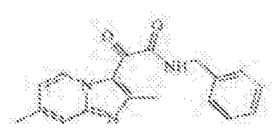 | 307.35 | $C_{19}H_{17}N_3O_2$ |
| ND-9630 | 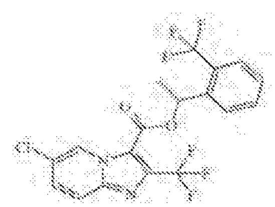 | 436.74 | $C_{22}H_{21}ClF_3N_3O_2$ |
| ND-9635 | 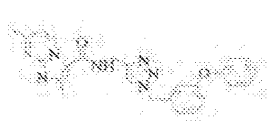 | 452.51 | $C_{26}H_{24}N_6O_2$ |

FIG. 4HH

| Compound ID | Structure | Mol Wt | Formula |
|---|---|---|---|
| ND-9653 | 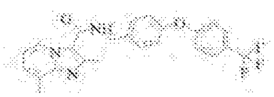 | 439.43 | C₂₃H₂₀F₃N₃O₂ |
| ND-9654 | 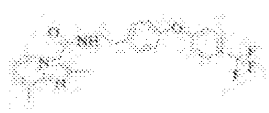 | 453.46 | C₂₄H₂₂F₃N₃O₂ |
| ND-9655 | 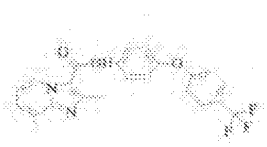 | 425.4 | C₂₂H₁₈F₃N₃O₂ |
| ND-9667 | | 309.29 | C₁₅H₁₂F₃N₃O |
| ND-9726 | 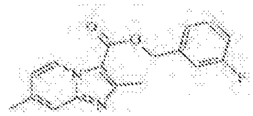 | 298.31 | C₁₇H₁₅FN₂O₂ |

FIG. 4II

| Compound ID | Structure | Mol Wt | Formula |
|---|---|---|---|
| ND-9727 | 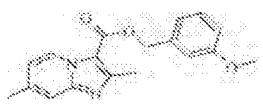 | 310.35 | $C_{19}H_{18}N_2O_2$ |
| ND-9728 | 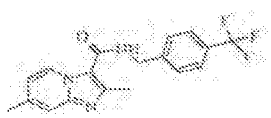 | 347.33 | $C_{19}H_{15}F_3N_2O$ |
| ND-9729 | 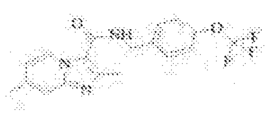 | 363.33 | $C_{19}H_{15}F_3N_2O_2$ |
| ND-9730 | 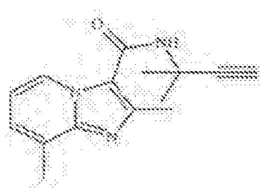 | 255.31 | $C_{15}H_{13}N_3O$ |
| ND-9731 | 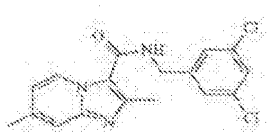 | 348.23 | $C_{17}H_{13}Cl_2N_3O$ |

FIG. 4JJ

| Compound ID | Structure | Mol Wt | Formula |
|---|---|---|---|
| ND-9733 | 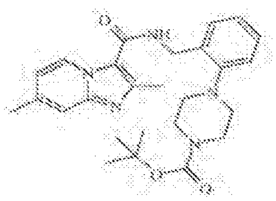 | 463.57 | $C_{29}H_{33}N_3O_3$ |
| ND-9734 | 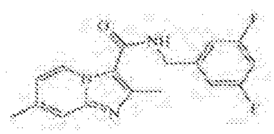 | 315.32 | $C_{17}H_{14}F_2N_2O$ |
| ND-9736 | | 297.33 | $C_{17}H_{15}FN_2O$ |
| ND-9739 | 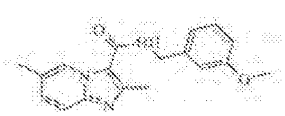 | 309.36 | $C_{18}H_{18}N_2O_2$ |
| ND-9740 | 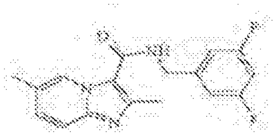 | 315.32 | $C_{17}H_{14}F_2N_2O$ |

FIG. 4KK

| Compound ID | Structure | Mol Wt | Formula |
|---|---|---|---|
| ND-9742 | 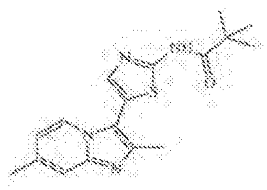 | 328.43 | C₁₇H₂₄N₄OS |
| ND-9755 | 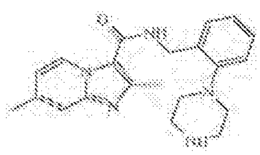 | 363.46 | C₂₃H₂₅N₃O |
| ND-9758 | 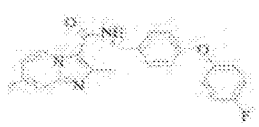 | 389.42 | C₂₃H₂₀FN₃O₂ |
| ND-9759 | 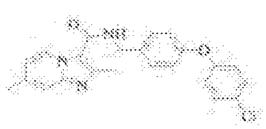 | 405.88 | C₂₃H₂₀ClN₃O₂ |
| ND-9760 | 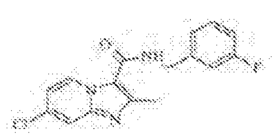 | 317.75 | C₁₇H₁₃ClFN₃O |

FIG. 4LL

| Compound ID | Structure | Mol Wt | Formula |
|---|---|---|---|
| ND-9761 | 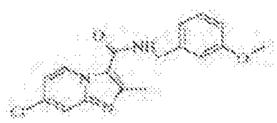 | 329.78 | C$_{17}$H$_{16}$ClN$_3$O$_2$ |
| ND-9766 | 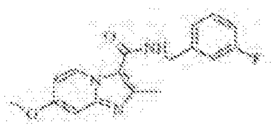 | 313.33 | C$_{17}$H$_{16}$FN$_3$O$_2$ |
| ND-9767 | 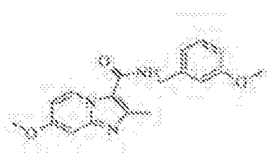 | 325.38 | C$_{18}$H$_{19}$N$_3$O$_3$ |
| ND-9768 | 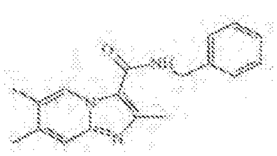 | 293.36 | C$_{19}$H$_{19}$N$_3$O |
| ND-9769 | 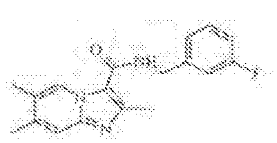 | 311.35 | C$_{18}$H$_{18}$FN$_3$O |

FIG. 4MM

| Compound ID | Structure | Mol Wt | Formula |
|---|---|---|---|
| ND-9770 | 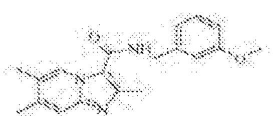 | 323.39 | $C_{19}H_{21}N_3O_2$ |
| ND-9872 | 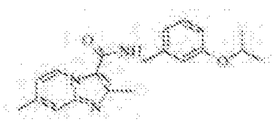 | 337.42 | $C_{20}H_{23}N_3O_2$ |
| ND-9873 | 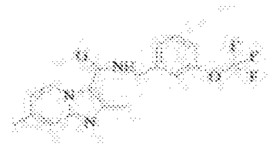 | 363.33 | $C_{19}H_{18}F_3N_3O_2$ |
| ND-9900 | 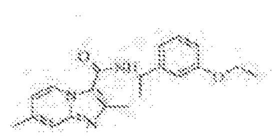 | 337.42 | $C_{20}H_{23}N_3O_2$ |
| ND-9901 | 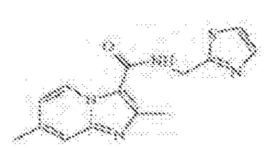 | 286.35 | $C_{15}H_{18}N_2OS$ |

FIG. 4NN

| Compound ID | Structure | Mol Wt | Formula |
|---|---|---|---|
| ND-9902 | 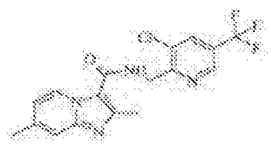 | 382.77 | C₁₇H₁₂ClF₃N₂O |
| ND-9903 | 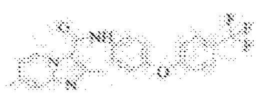 | 425.4 | C₂₀H₁₆F₃N₃O₂ |
| ND-9904 | 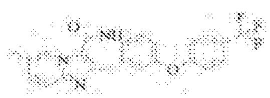 | 425.4 | C₂₀H₁₆F₃N₃O₂ |
| ND-9905 | 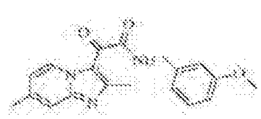 | 337.37 | C₁₉H₁₉N₃O₃ |
| ND-9906 | 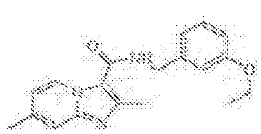 | 323.39 | C₁₉H₂₁N₃O₂ |

FIG. 40O
| Compound ID | Structure | Mol Wt | Formula |
|---|---|---|---|
| ND-9952 | 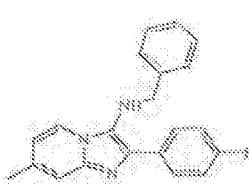 | 331.39 | $C_{22}H_{18}FN_3$ |
| ND-9953 | 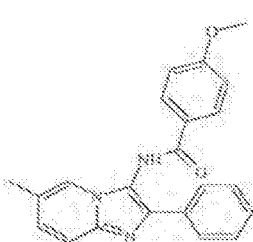 | 357.41 | $C_{23}H_{19}N_3O$ |
| ND-9954 | 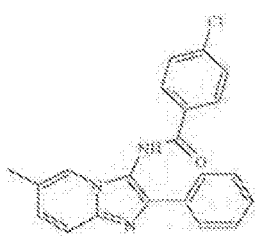 | 361.82 | $C_{22}H_{16}ClN_3O$ |
| ND-9985 | 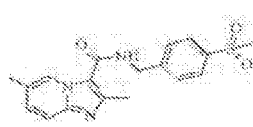 | 357.43 | $C_{17}H_{15}N_3O_3S$ |
| ND-10029 |  | 363.33 | $C_{19}H_{16}F_3N_3O_2$ |

FIG. 4PP

| Compound ID | Structure | Mol Wt | Formula |
|---|---|---|---|
| ND-10021 | 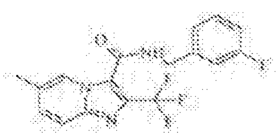 | 351.3 | $C_{17}H_{13}F_2N_3O$ |
| ND-10022 | 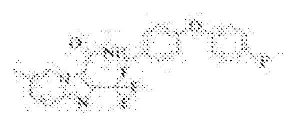 | 443.39 | $C_{23}H_{17}F_2N_3O_3$ |
| ND-10023 | 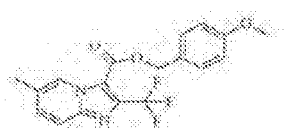 | 384.32 | $C_{19}H_{15}F_2N_3O_3$ |
| ND-10024 | 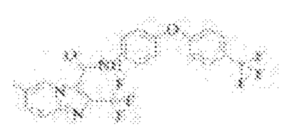 | 479.37 | $C_{23}H_{16}F_5N_3O_2$ |
| ND-10027 | 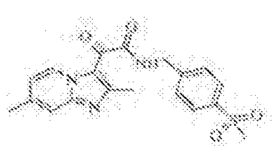 | 385.44 | $C_{19}H_{19}N_3O_3S$ |

FIG. 4QQ
| Compound ID | Structure | Mol Wt | Formula |
|---|---|---|---|
| ND-10028 | 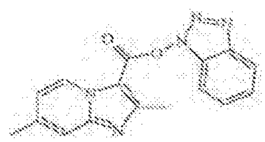 | 307.31 | C₁₉H₁₃NO₃ |
| ND-10029 | 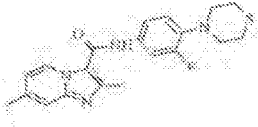 | 384.47 | C₂₂H₂₁FN₂OS |
| ND-10030 | 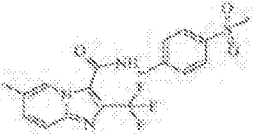 | 411.4 | C₂₀H₁₆F₄N₂O₂S |
| ND-10032 | 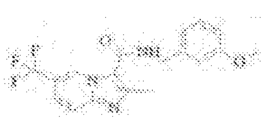 | 363.33 | C₁₉H₁₅F₃N₂O₂ |
| ND-10033 | 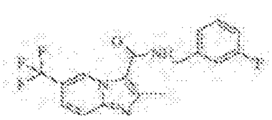 | 351.3 | C₁₈H₁₃F₃N₂O |

FIG. 4RR

| Compound ID | Structure | Mol Wt | Formula |
|---|---|---|---|
| ND-10034 | 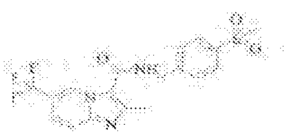 | 411.4 | $C_{19}H_{18}F_3N_2O_3S$ |
| ND-10035 | | 489.47 | $C_{22}H_{18}F_3N_2O_5S$ |
| ND-10038 | 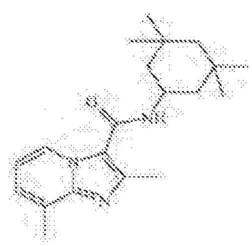 | 327.46 | $C_{21}H_{29}N_2O$ |
| ND-10046 | 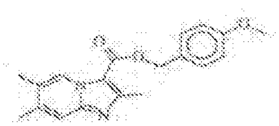 | 324.37 | $C_{19}H_{20}N_2O_3$ |
| ND-10047 | 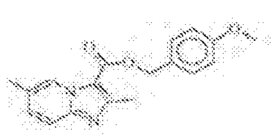 | 310.35 | $C_{18}H_{18}N_2O_3$ |

FIG. 4SS

| Compound ID | Structure | Mol Wt | Formula |
|---|---|---|---|
| ND-10053 | 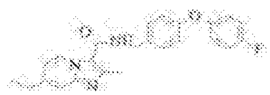 | 403.45 | $C_{22}H_{22}FN_3O_3$ |
| ND-10056 | 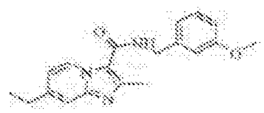 | 323.39 | $C_{19}H_{21}N_3O_2$ |
| ND-10058 | 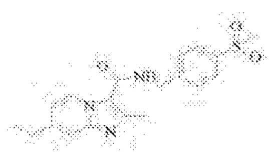 | 371.45 | $C_{19}H_{21}N_3O_3S$ |
| ND-10059 | 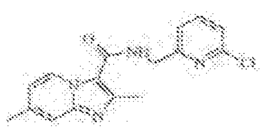 | 314.77 | $C_{17}H_{15}ClN_4O$ |
| ND-10060 | 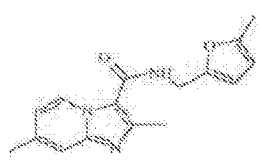 | 283.33 | $C_{15}H_{17}N_3O_2$ |

FIG. 4TT
| Compound ID | Structure | Mol Wt | Formula |
|---|---|---|---|
| ND-09650 | 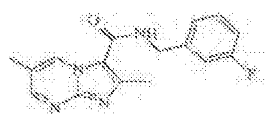 | 298.31 | $C_{16}H_{13}FN_4O$ |
| ND-09651 | 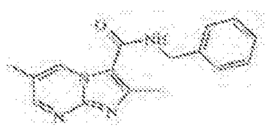 | 280.32 | $C_{18}H_{16}N_4O$ |
| ND-0862 |  | 310.35 | $C_{17}H_{18}N_4O_2$ |
| ND-10054 | 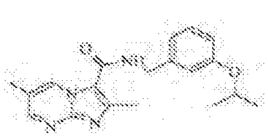 | 338.4 | $C_{19}H_{22}N_4O_2$ |
| ND-10057 | 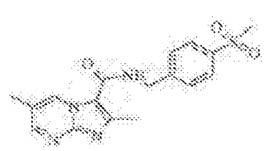 | 358.41 | $C_{17}H_{18}N_4O_3S$ |

US 9,908,876 B2

IMIDAZO [1,2-A]PYRIDINE COMPOUNDS, SYNTHESIS THEREOF, AND METHODS OF USING SAME

CROSS-REFERENCE TO RELATED APPLICATION

The present application claims priority to U.S. Provisional Patent Application No. 61/258,549, filed Nov. 5, 2009, entitled IMIDAZO[1,2-a] PYRIDINE COMPOUNDS, SYNTHESIS THEREOF, AND METHODS OF USING SAME, the disclosure of which is hereby incorporated by reference in its entirety.

GOVERNMENT INTERESTS

This invention was made with Government support under Grant R01 AI 054193 awarded by the National Institutes of Health. The Government has certain rights in the invention.

TECHNICAL FIELD

Embodiments herein relate to the field of chemistry and biochemistry, and, more specifically, to imidazo[1,2-a]pyridine compounds, synthesis thereof, and methods of using same.

BACKGROUND

Worldwide, over two billion people are infected with tuberculosis (TB), and an estimated 14,400,000 people have active cases of TB. Of these active cases, 83% are located in Africa, South-East Asia and the Western Pacific region. The global impact of TB is enormous: each year, TB kills 1.5 million HIV-negative people and 0.2 million HIV-positive people. New drug resistant strains emerge each year.

The current treatment for active, drug-susceptible TB includes a carefully-monitored regimen of a cocktail of rifampin, isoniazid, pyrazinamide and ethambutol for two months, followed by an additional four months of rifampin and isoniazid. Multi-drug resistant TB infection requires a lengthy course of therapy lasting two years or more with drugs that are expensive and poorly tolerated. Because of their length, complexity, and expense, these regimens represent inadequate therapies for most TB cases. New therapeutics are urgently needed to combat TB infection, yet no new drugs have been approved to treat TB in over 40 years.

In addition, in a different technical area, a large number of fungi are known to grow at the expense of commercially important plants that are essential to human survival. A number of fungicides have been developed for use in protecting both ornamental plants and food crops from pathogenic fungi. While many safe and effective fungicides are currently in use, the evolution of pathogenic fungi and the ever-increasing pressure to use lower levels of fungicides create the need for new fungicides. Effective antifungal treatments are urgently needed to treat damaging fungal infections in plant species.

BRIEF DESCRIPTION OF THE DRAWINGS

Embodiments will be readily understood by the following detailed description in conjunction with the accompanying drawings. Embodiments are illustrated by way of example and not by way of limitation in the figures of the accompanying drawings.

FIG. 2 shows the SAR of particular imidazo[1,2-a]pyridine agents and some trends observed from screening the compounds in an anti-TB assay.

FIG. 3 shows the SAR of particular imidazo[1,2-a]pyridine agents and some trends observed from screening the compounds in an antifungal assay.

FIG. 4 shows the structures of particular imidazo[1,2-a]pyridine agents screened in FIGS. 2 and 3.

DETAILED DESCRIPTION OF DISCLOSED EMBODIMENTS

Figure 1:
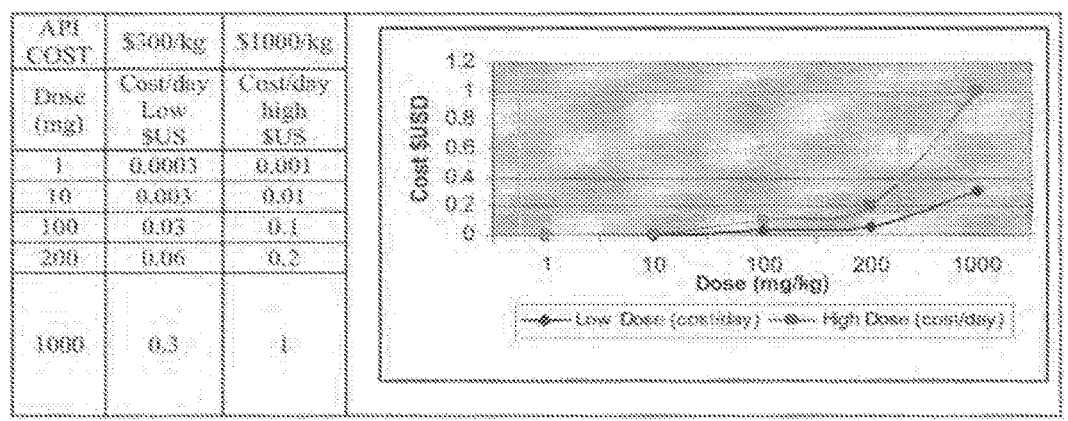
FIG. 1 illustrates the low cost of treatment with high- and low-dose imidazo[1,2-a]pyridine therapy for TB.

In the following detailed description, reference is made to the accompanying drawings which form a part hereof, and in which are shown by way of illustration embodiments that may be practiced. It is to be understood that other embodiments may be utilized and structural or logical changes may be made without departing from the scope. Therefore, the following detailed description is not to be taken in a limiting sense, and the scope of embodiments is defined by the appended claims and their equivalents.

Various operations may be described as multiple discrete operations in turn, in a manner that may be helpful in understanding embodiments; however, the order of description should not be construed to imply that these operations are order dependent.

For the purposes of the description, a phrase in the form "A/B" or in the form "A and/or B" means (A), (B), or (A and B). For the purposes of the description, a phrase in the form "at least one of A, B, and C" means (A), (B), (C), (A and B), (A and C), (B and C), or (A, B and C). For the purposes of the description, a phrase in the form "(A)B" means (B) or (AB) that is, A is an optional element.

The description may use the terms "embodiment" or "embodiments," which may each refer to one or more of the same or different embodiments. Furthermore, the terms "comprising," "including," "having," and the like, as used with respect to embodiments, are synonymous.

As used herein, the term "halogen" refers to fluoro, bromo, chloro, and iodo substituents.

As used herein, the term "alkyl" refers to a cyclic, branched, or straight chain alkyl group containing only carbon and hydrogen, and unless otherwise mentioned contains one to twelve carbon atoms. This term may be further exemplified by groups such as methyl, ethyl, n-propyl, isopropyl, isobutyl, t-butyl, pentyl, pivalyl, heptyl, adamantyl, and cyclopentyl. Alkyl groups can either be unsubstituted or substituted with one or more substituents, for instance, halogen, alkyl, alkoxy, alkylthio, trifluoromethyl, acyloxy, hydroxy, mercapto, carboxy, aryloxy, aryloxy, aryl, arylalkyl, heteroaryl, amino, alkylamino, dialkylamino, morpholino, piperidino, pyrrolidin-1-yl, piperazin-1-yl, or other functionality to form a "functionalized alkyl."

As used herein, the term "substituted alkyl" refers to an alkyl moiety including 1-4 substituents selected from halogen, het, cycloalkyl, cycloalkenyl, aryl, amino, cyano, nitro, —$OQ_{10}$, —$SQ_{10}$, —$S(O)_2Q_{10}$, —$S(O)Q_{10}$, —$OS(O)_2Q_{10}$, —$C(=NQ_{10})Q_{10}$, —$C(=NOQ_{10})O_{10}$, —$S(O)_2$—N=S(O)$(Q_{10})_2$, —$S(O)_2$—N=S$(Q_{10})_2$, —$NQ_{10}Q_{10}$, —$C(O)Q_{10}$, —$C(S)Q_{10}$, —$C(O)OQ_{10}$, —$OC(O)Q_{10}$, —$C(O)NQ_{10}Q_{10}$, —$C(S)NQ_{10}Q_{10}$, —$N(Q_{10})C(S)NQ_{10}Q_{10}$, —$C(O)NQ_{10}Q_{10}$, —$C(S)NQ_{10}Q_{10}$, —$C(O)C(Q_{10})_2OC(O)Q_{10}$, —CN, =S, —$NQ_{10}C(O)Q_{10}$, —$NQ_{10}C(O)NQ_{10}Q_{10}$, —$S(O)_2NQ_{10}Q_{10}$, —$NQ_{10}S(O)_2Q_{10}$, —$NQ_{10}S(O)Q_{10}$, —$NQ_{10}SQ_{10}$, and —$SNQ_{10}Q_{10}$. Each of the het, cycloalkyl, cycloalkenyl, and aryl being optionally substituted with 1-4 substituents independently selected from halogen and $Q_{15}$.

As used herein, the term "cycloalkyl" refers to a cyclic alkyl moiety. Unless otherwise stated, cycloalkyl moieties include between 3 and 8 carbon atoms.

As used herein, the term "alkene" refers to a hydrocarbon molecule with the general formula $C_nH_{2n}$ that contains one or more double bonds.

As used herein, the term "alkyne" refers to a moiety having the general formula $C_2H_{2n-2}$ corresponding to carbon chains with a triple carbon-carbon bond included.

As used herein, the term "alcohol" refers to any organic compound in which a hydroxyl group (—OH) is bound to a carbon atom of an alkyl or substituted alkyl group. The general formula for simple acyclic alcohols is $C_nH_{2n+1}OH$.

As used herein, the term "epoxide" refers to any of a class of organic compound, cyclic ethers, having a three-member ring.

As used herein, the term "ketone" refers to an organic compound containing the carbonyl group, >C=O, to which other carbon atoms are attached.

As used herein, the term "ester" refers to the product of the reaction between a carboxylic acid and an alcohol.

As used herein, the term "ether" refers to an organic compound containing the functional group RO—R'.

As used herein, the term "aldehyde" refers to an organic compound containing a —CHO group.

As used herein, the term "nitrile" refers to any of a class of organic compounds containing the cyano radical —CN.

As used herein, the term "thiol" refers to a molecular group that includes a bonded sulfur and hydrogen atom (—SH).

As used herein, the term "thioester" refers to a compound resulting from the bonding of sulfur with an acyl group with the general formula R—S—CO—R'. Thioesters are the product of esterification between a carboxylic acid and a thiol (as opposed to an alcohol in regular esters).

As used herein, the term "sulfide" refers to an organic compound containing sulfur bonded to carbon. The term "disulfide" refers to the structural unit composed of a linked pair of sulfur atoms.

As used herein, the term "sulfone" refers to a chemical compound containing a sulfonyl functional group attached to two carbon atoms. The central sulfur atom is twice double bonded to oxygen and has two further hydrocarbon substituents. The general structural formula is R—S(=O)(=O)—R' where R and R' are the organic groups.

As used herein, the term "sulfoxide" refers to a chemical compound containing a sulfinyl functional group attached to two carbon atoms. Sulfoxides can be considered oxidized sulfides.

As used herein, the term "amine" refers to $NH_2$, NHR, or $NR_2$. Unless otherwise stated R can be alkyl, alkenyl, alkynyl, cycloalkyl, cycloalkenyl, het or aryl.

As used herein, the term "amide" refers to an organic compound containing the —$CONH_2$— group.

As used herein, the term "urea" refers to an organic compound with the chemical formula $(NH_2)_2$ CO or RNHCONHR'.

As used herein, the term "carbamate" refers to any of a group of organic compounds sharing a common functional group with the general structure —NH(CO)O—. Carbamates are esters of carbarnic acid, $NH_2COOH$. Since carbarnic acid contains nitrogen attached to a carboxyl group, it is also an amide. Therefore, carbamate esters may have alkyl or aryl groups substituted on the nitrogen, or the amide function.

For example, ethyl carbamate is unsubstituted, whereas ethyl N-methylcarbamate has a methyl group attached to the nitrogen.

As used herein, the term "nitro" refers to $NO_2$.

As used herein, the term "aryl" refers to phenyl, substituted phenyl, naphthyl, and substituted naphthyl.

As used herein, the term "morpholine" refers to an organic chemical compound having the chemical formula $O(CH_2CH_2)_2NH$. This heterocycle features both amine and ether functional groups. Because of the amine, morpholine is a base; its conjugate acid is called morpholinium. For example, when morpholine is neutralized by hydrochloric acid, one obtains the salt morpholinium chloride.

As used herein, the term "thiomorpholine" refers to $C_4H_9NS$, and is a heterocyclic compound containing nitrogen and sulfur. It may be considered a thio derivative of morpholine.

As used herein, the term "piperazine" refers to an organic compound that consists of a six-member ring containing two opposing nitrogen atoms.

As used herein, the term "piperidine" refers to an organic compound with the molecular formula $(CH_2)_5NH$. This heterocyclic amine consists of a six-member ring containing five methylene units and one nitrogen atom.

As used herein, the term "acyl" refers to any of a group or radical of the form RCO— where R is an organic group.

As used herein, the term "furan" refers to any of a class of aromatic heterocyclic compounds containing a ring of four carbon atoms and an oxygen atom; for instance, $C_4H_4O$. As used herein, the term "nitrofuran" refers to a furan ring with a nitro group.

As used herein, the term "thiophene" refers to the heterocyclic compound with the formula $C_4H_4S$. Consisting of a flat five-membered ring, it is aromatic as indicated by its extensive substitution reactions. Related to thiophene are benzothiophene and dibenzothiophene, containing the thiophene ring fused with one and two benzene rings, respectively. Compounds analogous to thiophene include furan ($C_4H_4O$) and pyrrole ($C_4H_4NH$).

As used herein, the term "imidazole" refers to an organic compound with the formula $C_3H_4N_2$. This aromatic heterocyclic is classified as an alkaloid. Imidazole refers to the parent compound whereas imidazoles are a class of heterocycles with similar ring structure but varying substituents. A nitroimidazole is an imidazole derivative that contains a nitro group.

As used herein, the term "oxazole" refers to a five-member heterocycle having three carbon atoms, one oxygen atom, one nitrogen atom and two double bonds; the 1,3-isomer is aromatic.

As used herein, the term "oxazoline" refers to an unsaturated heterocyclic compound containing a five-member ring, two double bonds, one nitrogen and one oxygen atom; and any derivative of this compound.

As used herein, the term "thiazole" refers to any of a class of unsaturated heterocyclic compounds containing a ring of three carbon atoms, a sulfur and an nitrogen atom; for instance the simplest one, $C_3H_3SN$.

As used herein, the term "thiazoline" refers to an unsaturated heterocyclic compound containing a five-member ring, two double bonds, one nitrogen and one sulfur atom; and any derivative of this compound.

As used herein, the term "triazole" refers to either one of a pair of isomeric chemical compounds with molecular formula $C_2H_3N_3$, having a five-member ring of two carbon atoms and three nitrogen atoms.

As used herein, the term "pyridine" refers to any of a class of aromatic heterocyclic compounds containing a ring of five carbon atoms and a nitrogen atom; for instance the simplest one, $C_5H_5N$.

As used herein, the term "pyrazine" refers to a diazine in which the two nitrogen atoms are in the para-position.

As used herein, the term "naphthalene" refers to an aromatic, white, solid hydrocarbon with formula $C_{10}H_8$ and the structure of two fused benzene rings.

As used herein, the term "diketopiperazine" refers to a class of cyclic organic compounds that result from peptide bonds between two amino acids to form a lactam. They are the smallest possible cyclic peptides.

As used herein, the term "quinoline" refers to any of a class of aromatic heterocyclic compounds containing a benzene ring fused with a ring of five carbon atoms and a nitrogen atom; for instance the simplest one, $C_9H_7N$. Isoquinoline, also known as benzo[c]pyridine or 2-benzanine, is a heterocyclic aromatic organic compound. It is a structural isomer of quinoline. Isoquinoline and quinoline are benzopyridines, which are composed of a benzene ring fused to a pyridine ring. In a broader sense, the term isoquinoline is used to make reference to isoquinoline derivatives.

As used herein, the term "oxazolidinone" refers to a class of heterocyclic organic compounds containing both nitrogen and oxygen in a 5-member ring.

As used herein, the term "heterocyclic" refers to organic compounds containing at least one atom of carbon, and at least one element other than carbon, such as sulfur, oxygen or nitrogen within a ring structure. These structures may comprise either simple aromatic rings or non-aromatic rings. Each mono-cyclic ring may be aromatic, saturated or partially unsaturated. A bi-cyclic ring system may include a mono-cyclic ring containing one or more heteroatom fused with a cycloalkyl or aryl group. A bi-cyclic ring system may also include a mono-cyclic ring containing one or more heteroatom fused with another mono-cyclic ring system.

Examples of "heterocyclics" include but are not limited to pyridine, thiophene, furan, pyrazoline, pyrimidine, 2-pyridyl, 3-pyridyl, 4-pyridyl, 2-pyrimidinyl, 4-pyrimidinyl, 5-pyrimidinyl, 3-pyrazinyl, 3-pyridazinyl, 4-pyridazinyl, 4-oxo-2-imidazolyl, 1,2,4-oxadiazole, 1,3,4-oxadiazole, 4-pyridazinyl, 3-pyrazinyl, 4-oxo-2-imidazolyl, 2-imidazolyl, 4-imidazolyl, 3-isoxazolyl, 4-isoxazolyl, 5-isoxazolyl, 3-pyrazolyl, 4-pyrazolyl, 5-pyrazolyl, 2-oxazolyl, 4-oxazolyl, 4-oxo-2-oxazolyl, 5-oxazolyl, 1,2,3-oxathiazole, 1,2,3-oxadiazole, 1,2,5-oxadiazole, 2-thiazolyl, 5-thiazolyl, 3-isothiazole, 4-isothiazole, 5-isothiazole, 2-furanyl, 3-furanyl, 2-thienyl, 3-thienyl, 2-pyrrolyl, 3-pyrrolyl, 3-isopyrrolyl, 4-isopyrrolyl, 5-isopyrrolyl, 1,2,3-oxathiazole-1-oxide, 1,2,4-oxadiazol-3-yl, 1,2,4-oxadiazol-5-yl, 5-oxo-1,2,4-oxadiazol-3-yl, 1,2,4-thiadiazol-3-yl, 1,2,4-thiadiazol-5-yl, 3-oxo-1,2,4-thiadiazol-5-yl, 1,3,4-thiadiazol-5-yl, 2-oxo-1,3,4-thiadiazol-5-yl, 1,2,4-triazol-3-yl, 1,2,4-triazol-5-yl, 1,2,3,4-tetrazol-5-yl, 5-oxazolyl, 3-isothiazolyl, 4-isothiazolyl, 5-isothiazolyl, 1,3,4-oxadiazole, 4-oxo-2-thiazolinyl, 5-methyl-1,3,4-thiadiazol-2-yl, thiazoledione, 1,2,3,4-thiatriazole, 1,2,4-dithiazolone, phthalimide, quinolinyl, morpholinyl, benzimidazolyl, benzo[d]thiazolyl, benzo[d]oxazolyl, diazinyl, triazinyl, quinolinyl, quinoxalinyl, naphthyridinyl, azetidinyl, pyrrolidinyl, hydantoinyl, oxathiolanyl, dioxolanyl, imidazolidinyl, azabicyclo [2.2.1] heptyl, 2-methyl-1,4-dioxa-8-azaspiro[4.5]decane, 2,3-dimethyl-1,4-dioxa-8-azaspiro[4.5]decane, 3-methyl-1,5-dioxa-9-azaspiro[5.5]undecane, and 2,4-dimethyl-1,5-dioxa-9-azaspiro[5.5]undecane.

As used herein, the term "heteroaryl" refers to a mono- or bicyclic het in which one or more cyclic ring is aromatic.

As used herein, the term "substituted heteroaryl" refers to a heteroaryl moiety substituted with one or more functional groups selected from halogen, alkyl, hydroxyl, amino, alkoxy, cyano, and nitro.

As used herein, the term "substituted aryl" refers to an aryl moiety having 1-3 substituents selected from halogen, het, alkyl, substituted alkyl, alkenyl, alkynyl, alkoxy, cycloalkyl, cycloalkenyl, aryl, cyano, nitro, $-OQ_{10}$, $-SO_{10}$, $-S(O)_2O_{10}$, $-S(O)Q_{10}$, $-OS(O)_2Q_{10}$, $-C(=NQ_{10})Q_{10}$, $-C(=NOQ_{10})Q_{10}$, $-S(O)_2-N=S(O)(Q_{10})_2$, $-S(O)_2-N=S(Q_{10})_2$, $-NQ_{10}Q_{10}$, $-C(O)Q_{10}$, $-C(S)Q_{10}$, $-C(O)OQ_{10}$, $-OC(O)Q_{10}$, $-C(O)NQ_{10}Q_{10}$, $-C(S)NQ_{10}Q_{10}$, $-C(O)C(Q_{10})_2OC(O)Q_{10}$, $-NQ_{10}C(O)Q_{10}$, $-N(Q_{10})C(S)NQ_{10}Q_{10}$, $-N(Q_{10})C(S)Q_{10}$, $-NQ_{10}C(O)NQ_{10}Q_{10}$, $-S(O)_2NQ_{10}Q_{10}$, $-NQ_{10}S(O)_2Q_{10}$, $-NQ_{10}S(O)Q_{10}$, $-NQ_{10}SQ_{10}$, and $-SNQ_{10}Q_{10}$. The het, cycloalkyl, cycloalkenyl, alkenyl, alkynyl, and aryl being optionally substituted with 1-3 substituents selected from halogen and $Q_{15}$.

Each $Q_{10}$ is independently selected from H, alkyl, cycloalkyl, het, cycloalkenyl, and aryl. The het, cycloalkyl, cycloalkenyl, and aryl being optionally substituted with 1-3 substituents selected from halo and $Q_{13}$.

Each $Q_{11}$ is independently selected from H, halogen, alkyl, aryl, cycloalkyl, and het. The alkyl, aryl, cycloalkyl, and het being optionally substituted with 1-3 substituents independently selected from halogen, nitro, cyano, $=S$, $=O$, and $Q_{14}$.

Each $Q_{13}$ is independently selected from $Q_{11}$, $-OQ_{11}$, $-SQ_{11}$, $-S(O)_2Q_{11}$, $-S(O)Q_{11}$, $-OS(O)_2Q_{11}$, $-C(=NQ_{11})O_{11}$, $-S(O)_2-N=S(O)(Q_{11})_2$, $-S(O)_2-N=S(Q_{11})_2$, $-SC(O)Q_{11}$, $-NQ_{11}Q_{11}$, $-C(O)Q_{11}$, $-C(S)Q_{11}$, $-C(O)OQ_{11}$, $-OC(O)Q_{11}$, $-C(O)NQ_{11}Q_{11}$, $-(S)NQ_{11}Q_{11}$, $-C(O)C(Q_{16})_2OC(O)Q_{10}$, $-CN$, $=O$, $=S$, $-NQ_{11}C(O)Q_{11}$, $-NQ_{11}C(S)Q_{11}$, $-NQ_{11}C(O)NQ_{11}Q_{11}$, $-NQ_{11}C(S)NQ_{11}Q_{11}$, $-S(Q)_2NQ_{11}Q_{11}$, $-NQ_{11}S(O)_2Q_{11}$, $-NQ_{11}S(O)Q_{11}$, $-NQ_{11}SQ_{11}$, $-NO_2$, and $-SNQ_{11}Q_{11}$.

Each $Q_{14}$ is independently selected from H, alkyl, cycloalkyl, phenyl, or naphthyl, each optionally substituted with 1-4 substituents independently selected from F, Cl, Br, I, $-OQ_{16}$, $-SQ_{16}$, $-S(O)_2O_{16}$, $-S(O)Q_{16}$, $-OS(O)_2Q_{16}$, $-NQ_{16}Q_{16}$, $-C(O)Q_{16}$, $-C(S)Q_{16}$, $-C(O)OQ_{16}$, $-NO_2$, $-C(O)NQ_{16}Q_{16}$, $-C(S)NQ_{16}Q_{16}$, $_{16}Q_{16}$, $-CN$, $-NQ_{16}C(O)Q_{16}$, $-NQ_{16}C(S)Q_{16}$, $-NQ_{16}C(O)NQ_{16}Q_{16}$, $-NQ_{16}C(S)NQ_{16}Q_{16}$, $-S(O)_2NQ_{16}Q_{16}$, and $-NQ_{16}S(O)_2Q_{16}$. The alkyl, cycloalkyl, and cycloalkenyl being further optionally substituted with $=O$ or $=S$.

Each $Q_{15}$ is independently selected from H, alkyl, cycloalkyl, heteroaryl, phenyl, or naphthyl, each optionally substituted with 1-4 substituents independently selected from F, Cl, Br, I, $-OQ_{16}$, $-SQ_{16}$, $-S(O)_2Q_{16}$, $-S(O)Q_{16}$, $-OS(O)_2Q_{16}$, $-C(=NQ_{16})Q_{16}$, $-S(O)_2-N=S(O)(Q_{16})_2$, $-S(O)_2-N=S(Q_{16})_2$, $-SC(O)Q_{16}$, $-NQ_{16}Q_{16}$, $-C(O)Q_{16}$, $-C(S)Q_{16}$, $-C(O)OQ_{16}$, $-OC(O)Q_{16}$, $-C(S)NQ_{16}Q_{16}$, $-C(O)C(Q_{16})_2OC(O)Q_{16}$, $-CN$, $-NQ_{16}C(O)Q_{16}$, $-NQ_{16}C(S)Q_{16}$, $-NQ_{16}C(O)NQ_{16}Q_{16}$, $-NQ_{16}C(S)NQ_{16}Q_{16}$, $-S(O)_2NQ_{16}Q_{16}$, $-NQ_{16}S(O)_2Q_{16}$, $-NQ_{16}S(O)Q_{16}$, $-NQ_{16}SQ_{16}$, $-NO_2$, and $-SNQ_{16}O_{16}$. The alkyl, cycloalkyl, and cycloalkenyl being further optionally substituted with $=O$ or $=S$.

Each $Q_{16}$ is independently selected from H, alkyl, and cycloalkyl. The alkyl and cycloalkyl optionally including 1-3 halogens.

Embodiments of the present disclosure provide novel imidazopyridines, for instance imidazo[1,2-a]pyridines.

Certain embodiments are directed to compounds and methods for the treatment and prevention of tuberculosis (TB). Other embodiments are directed to compounds and methods for inhibiting fungal growth on plant species. In still other embodiments, methods are provided for the synthesis of the disclosed imidazo[1,2-a]pyridine compounds.

In embodiments, the imidazo[1,2-a]pyridine compounds of this disclosure may be useful in treating or preventing tuberculosis in a subject. The in vitro activity of disclosed compounds may be assessed by standard testing procedures, for instance in H37Rv TB screens.

In embodiments, the imidazo[1,2-a]pyridine compounds described herein may be useful for treating (for instance, ameliorating or preventing) multi-drug resistant (MDR) and non-MDR TB in a subject. In an embodiment, a compound may be administered to a subject locally or systemically. In embodiments, an imidazo[1,2-a]pyridine compound may be administered parenterally, for instance subcutaneously, intravenously, or intramuscularly, or it may be administered orally or by inhalation. An imidazo[1,2-a]pyridine compound may be used alone or in combination with other anti-tuberculosis agents. In an embodiment, an imidazo[1,2-a]pyridine compound may be administered in varying concentrations depending upon the infection's susceptibility to the compound being administered, the extent of the disease, whether the infection is latent or active, whether the infection is drug-resistant, and the general health of the subject.

In an embodiment, imidazo[1,2-a]pyridine compounds may be incorporated into a pharmaceutical composition. Embodiments of the present disclosure encompass any racemic, optically-active, polymorphic, tautomeric, or stereoisomeric form or mixture thereof, of a compound of the disclosure, which possesses the useful properties described herein.

In cases where compounds are sufficiently basic or acidic to form stable nontoxic acid or base salts, use of the compounds as pharmaceutically acceptable salts may be appropriate. Examples of pharmaceutically acceptable salts within the scope of embodiments herein include organic acid addition salts formed with acids which form a physiological acceptable anion and inorganic salts.

Pharmaceutical compositions in accordance with embodiments of the disclosure may be prepared by combining the disclosed compounds with a solid or liquid pharmaceutically acceptable carrier and, optionally, with pharmaceutically acceptable adjuvants and excipients employing standard and conventional techniques. Solid form compositions include powders, tablets, dispersible granules, capsules, cachets and suppositories. A solid carrier may be at least one substance that may also function as a diluent, flavoring agent, solubilizer, lubricant, suspending agent, binder, tablet disintegrating agent, and encapsulating agent. Inert solid carriers include magnesium carbonate, magnesium stearate, talc, sugar, lactose, pectin, dextrin, starch, gelatin, cellulosic materials, low melting wax, cocoa butter, and the like. Liquid form compositions include solutions, suspensions and emulsions. For example, there may be provided solutions of the compounds disclosed herein dissolved in water and water-propylene glycol systems, optionally containing suitable conventional coloring agents, flavoring agents, stabilizers, and/or thickening agents.

In an embodiment, a pharmaceutical composition may be provided employing conventional techniques in unit dosage form containing effective or appropriate amounts of one or more active component. In embodiments, the quantity of active component (compound) in a pharmaceutical composition and unit dosage form thereof may be varied or adjusted widely depending upon the particular application, the potency of the particular compound and the desired concentration. In an embodiment, the quantity of active component may range from 0.5% to 90% by weight of the composition.

In embodiments, in therapeutic use for treating, ameliorating, preventing, or combating TB in subjects, the compounds or pharmaceutical compositions thereof may be administered orally, parenterally, and/or by inhalation at a dosage to obtain and maintain a concentration or blood-level of active component in the animal undergoing treatment that is therapeutically effective. In an embodiment, such a therapeutically effective amount/dosage of active component may be in the range of from about 0.1 to about 100 mg/kg, for instance, from about 0.1 to about 10 mg/kg, of body weight/day. It is to be understood that the dosages may vary depending upon the requirements of the patient, the severity of the infection, the particular mycobacterial species, whether the infection is latent or active, the drug resistance of the strain, the duration of the infection being treated, and the particular compound being used. Also, it is to be understood that the initial dosage administered may be increased beyond the above upper level in order to rapidly achieve the desired blood-level or the initial dosage may be smaller than the optimum and the daily dosage may be progressively increased during the course of treatment depending on the particular situation. If desired, the daily dose also may be divided into multiple doses for administration, for instance, two to four times per day.

In an embodiment, an initial imidazo[1,2-a]pyridine compound was provided and tested as an exemplary member of the new imidazo[1,2-a]pyridine class of anti-tuberculosis agents disclosed herein. Such compound is identified below as compound ND-8454, and the compound's structure is shown in Table 1. Imidazo[1,2-a]pyridine is a simple bicyclic compound with a bridgehead nitrogen atom. This class of molecules is unrepresented within the TB literature, and the scaffold is very attractive because of the low cost of starting materials and the ease with which potent (<1 µg/mL) anti-TB compounds are synthesized therefrom.

Many of the existing clinical candidates for TB therapeutics are derivatives of existing scaffolds (for instance, moxifloxacin and gatifloxacin, see Table 1), which results in drugs that are much more prone to emerging resistance. Other clinical candidates are complex compounds that are difficult and costly to manufacture (for example anti-TB candidates TMC207, PA-824, OPC-67683, and LL-3858, see Table 1).

In contrast, ND-8454, N-benzyl-2,7-dimethylimidazo[1,2-a]pyridine-3-carboxamide, the initial "hit" based on the imidazo[1,2-a]pyridine scaffold, has an in vitro activity against H37Rv TB comparable to the current clinical candidates (MIC=0.08 µg/mL or 286 nM) and no observed toxicity to VERO or HeLa cells (>128 and >50 µM, respectively).

TABLE 1

Current TB clinical candidates and ND-8454
(initial imidazo[1,2-a]pyridine hit)

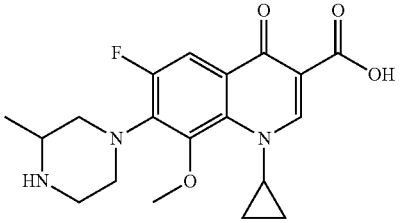

Gatifloxacin (OFLOTUB Consortium)
MIC = 0.03-1.56 µg/mL H37Rv TB
MIC = 3.12 µg/mL MDR-TB
LD99 = 0.5 µg/mL

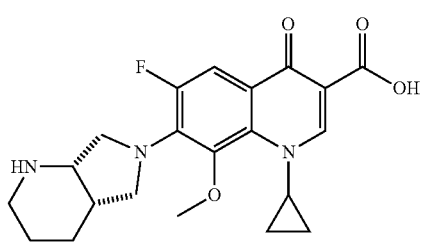

Moxifloxacin (Bayer)
MIC = 0.04-0.5 µg/mL H37Rv TB
MIC = 0.5 µg/mL MDR-TB
LD99 = 0.8 µg/mL

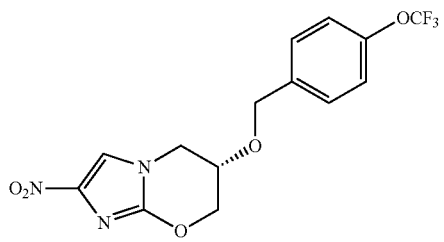

PA-824 (TB Alliance)
MIC of 0.25-0.03 µg/mL
vs. H37Rv and MDR-TB

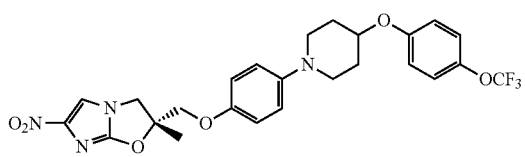

OPC-67683 (Otsuka)
MIC of 0.006-0.024 µg/mL
vs. H37Rv and MDR-TB

TABLE 1-continued

Current TB clinical candidates and ND-8454
(initial imidazo[1,2-a]pyridine hit)

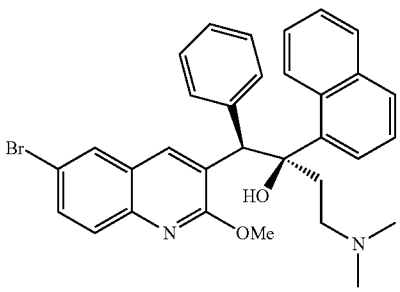

TMC207 (Diarylquinoline, J & J)
MIC = 0.06 µg/mL vs H37Rv and MDR-TB

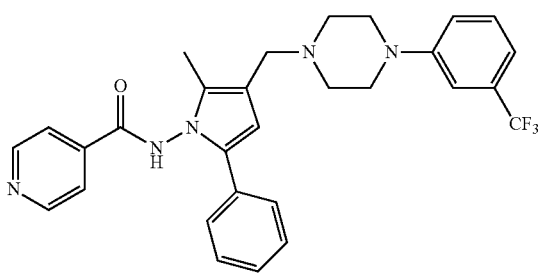

LL-3858 (Sudoterb, Lupin)
MIC = 0.06 µg/mL

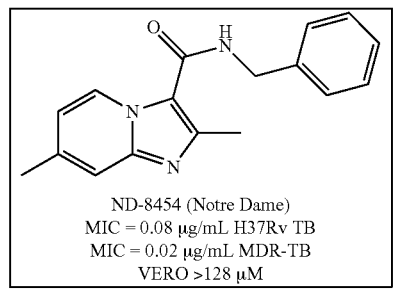 [SMILES: Cc1ccn2c(C(=O)NCc3ccccc3)c(C)nc2c1]

ND-8454 (Notre Dame)
MIC = 0.08 µg/mL H37Rv TB
MIC = 0.02 µg/mL MDR-TB
VERO >128 µM In accordance with various embodiments, Table 2 illustrates the potency of several exemplary compounds against several individual strains of single drug resistant TB.

TABLE 2

TB Potency against single drug resistant strains (MIC90 in µM)

| Resistance to (µM) | rRMP | rINH | rKM | rSM |
|---|---|---|---|---|
| ND-8454 | 0.28 | 0.33 | 1.07 | 1.02 |
| ND-9652 | 1.49 | 2.03 | 5.83 | 5.84 |
| ND-9758 | <0.002 | 0.003 | 0.01 | 0.01 |
| ND-9872 | 0.23 | 0.28 | 0.89 | 0.87 |
| ND-9902 | 0.74 | 1.10 | 2.96 | 2.95 |
| ND-9903 | 0.24 | 0.25 | 0.59 | 0.63 |
| ND-9965 | 0.54 | 0.57 | 1.98 | 2.31 |
| RMP | >1 | 0.01 | 0.02 | 0.02 |
| INH | 0.23 | >8 | 0.43 | 0.23 |
| MOX | 0.10 | 0.12 | 0.24 | 0.15 |

RMP = Rifampicin;
INH—Isoniazid;
KM = Kanamycin;
SM = Streptomycin

In accordance with various embodiments, Table 3 illustrates the potency of several exemplary compounds against several strains of multi-drug resistant (MDR) TB.

TABLE 3

| | MDR-TB Potency (MIC90 in μg/mL) | | | | | | | | |
|---|---|---|---|---|---|---|---|---|---|
| | Resistance to (μg/mL): | | | | | | | | |
| | HRESP | HREZSP | HCPTh | HREKP | HRERb* | HREZSKPTh | HRERb* | HRERb* | HREZRbTh |
| ND-8454 | 0.625 | 0.3125 | 0.313 | 0.078 | 0.039 | 0.019 | 0.039 | 0.078 | 0.039 |
| ND-8667 | 0.3125 | 0.019 | 0.039 | 0.039c | <=0.0098 | <=0.0098 | 0.01 | 0.019 | 0.019 |
| ND-9361 | 0.078 | 0.019 | NT | 0.078 | 0.039 | 0.019 | 0.01 | 0.078 | 0.019 |

Abbreviations:
H = Isoniazid,
R = Rifampicin,
E = Ethambutol,
Z = Pyrazinamide,
S = Streptomycin,
C = Cycloserine,
K = Kanamycin,
P = p-aminosalicylic acid,
Rb = rifabutin,
Th = thioacetazone,
*genetically different strains.

In embodiments, the exemplary compounds described above may be synthesized according to the following general procedures. ND-8454, for example, can be made in four synthetic steps from readily available, inexpensive reagents. To evaluate the potential availability and affordability of making this compound on a kilogram scale, the cost to scale up ND-8454 using the following exemplary procedure was evaluated (see Scheme 1, below).

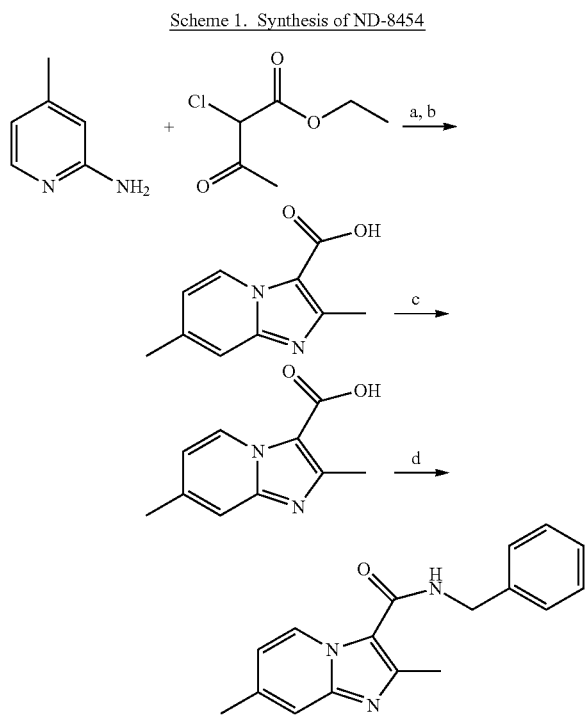

Scheme 1. Synthesis of ND-8454

Reagents:
(a) 1,2-dimethoxyethane, reflux, 48 hours;
(b) 1N LiOH, EtOH, reflux, 36 hours;
(c) oxalyl chloride, $CH_2Cl_2$, DMF (cat.), room temperature, 4 hours;
(d) benzylamine, $Et_3N$, $CH_2Cl_2$, reflux, 14 hours In this specific example of synthesis of ND-8454, a solution of 2-amino-4-picoline (10.0 g, 91.5 mmol) and ethyl-2-chloroacetoacetate (7.93 g, 45.8 mmol) were dissolved in 92 mL of 1,2-dimethoxyethane (DME) and heated for 36 h at reflux. The reaction mixture was filtered and solids (2-amino-4-picoline hydrochloride salt) was collected and washed with hexanes. The filtrate liquor was concentrated in vacuo and residue was dissolved in $CH_2Cl_2$ and washed with 5% acetic acid solution (2×) and brine. The organic phase was collected, dried over sodium sulfate ($Na_2SO_4$), filtered and then concentrated in vacuo. Crude material obtained was purified by silica gel column chromatography with a 20% ethyl acetate: $CH_2Cl_2$ solvent system to give 7.8 g (78%) of ethyl 2,7-dimethylimidazo[1,2-a]pyridine-3-carboxylate as a tan solid. mp 59-61° C.; $^1$H NMR (300 MHz, $CDCl_3$) 9.14 δ (d, J=7.1 Hz, 1H), 7.34 (s, 1H), 6.78 (dd, J=7.1, 1.7 Hz, 1H), 4.40 (q, J=7.1, 7.1, 7.1 Hz, 2H), 2.66 (s, 3H), 2.42 (s, 3H), 1.42 (t, J=7.1, 7.1 Hz, 3H). HRMS (EI), M+1 calcd. for $C_{12}H_{15}N_2O_2$, 219.1155. found 219.1128. Retention time=1.4 minutes (mobile phase: 60% water: acetonitrile).

The ethyl 2,7-dimethylimidazo[1,2-a]pyridine-3-carboxylate (6.4 g, 29.3 mmol) was dissolved in 75 mL of ethanol (95%), 1M LiOH (60 mL, 60 mmol) was added and reaction was heated to reflux for 36 hours. The resulting solution was concentrated to dryness and then made acidic (pH-2-3) with the addition of 4 N HCl; resulting solids were collected by filtration and rigorously dried to give 4.6 grams (82%) of 2,7-dimethylimidazo[1,2-a]pyridine-3-carboxylic acid, an off-white solid. mp 180-183° C.; $^1$H NMR (300 MHz, $CD_3OD$) δ 9.52 (d, J=7.1 Hz, 1H), 7.73 (td, J=1.8, 0.9, 0.9 Hz, 1H), 7.48 (dd, J=7.1, 1.3 Hz, 1H), 2.81 (s, 3H), 2.63 (s, 3H). HRMS (EI), M+1 calcd. for $C_{10}H_{11}N_2O_2$, 191.0815. found 191.0837. Retention time=0.6-0.7 minutes (mobile phase: 60% water:acetonitrile).

The 2,7-dimethylimidazo[1,2-a]pyridine-3-carboxylic acid (2.8 grams, 14 mmol) was partly dissolved in 35 mL anhydrous $CH_2Cl_2$ and oxalyl chloride (3.3 mL, 39 mmol) was added followed by catalytic (20 μL) N'N-dimethylformamide (DMF).

The reaction was stirred under argon at room temperature for 4 hours. The clear, orange solution was concentrated to dryness and the resulting acid chloride (3.6 grams, 14 mmol, yellow solid) was dissolved in 35 mL anhydrous $CH_2Cl_2$. Triethylamine (5.9 mL, 41.9 mmol) and benzylamine (1.8 mL, 16.7 mmol) were added slowly. The reaction was heated to 50° C. under argon for 16 hours. The reaction was then concentrated to dryness and the resulting solid was dissolved in ethyl acetate (EtOAc) and washed with saturated sodium bicarbonate solution (2×) and brine washed.

The organics were collected and dried over $Na_2SO_4$, the drying agent was filtered off, and the organics were concentrated down to an oil which crystallized upon standing. The solid was purified through a silica gel column eluting with a gradient of 1:10 (EtOAc:$CH_2Cl_2$) to 10:1 (EtOAc:$CH_2Cl_2$). 2.75 grams of N-benzyl-2,7-dimethylimidazo[1,2-a]pyridine-3-carboxamide (ND-8454, 70%) was obtained as an off-white solid. mp 166-167° C.; $^1$H NMR (500 MHz, $CDCl_3$) δ 9.30 (d, J=7.1 Hz, 1H), 7.39-7.28 (m, 5H), 7.25 (s, 1H), 6.75 (dd, J=7.2, 1.8 Hz, 1H), 6.05 (bs, 1H, NH), 4.69 (d, J=5.7 Hz, 2H), 2.65 (s, 3H), 2.41 (s, 3H). $^{13}$C NMR (126 MHz, $CDCl_3$) δ 161.52, 146.54, 145.36, 138.30, 128.84, 127.67, 127.61, 127.35, 127.31, 115.72, 115.05, 43.42, 21.34, 16.83. HRMS (EI), M+1 calcd. for $C_{17}H_{18}N_3O$, 280.1444. found 280.1480. Retention time=0.8-1.1 minutes (mobile phase: 60% water:acetonitrile).

In another embodiment, imidazo[1,2-a]pyridine compounds may be synthesized according to the general procedures shown in Scheme 2, below.

Scheme 2: Imidazo[1,2-a]pyridine Chemistry

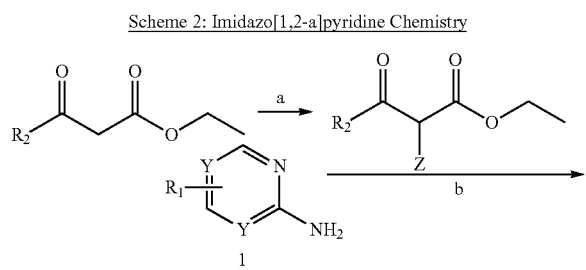

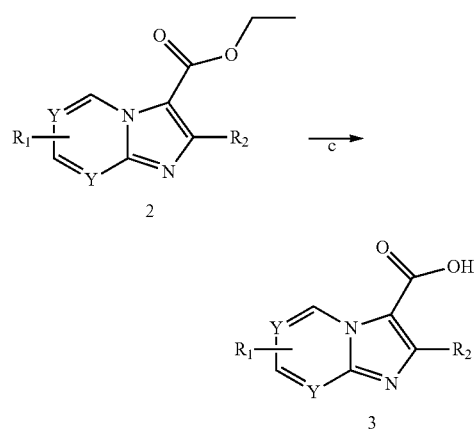

Analog generation:

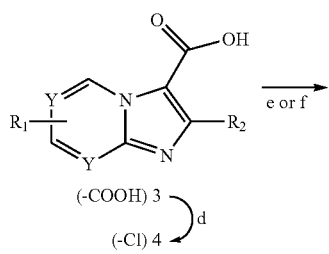

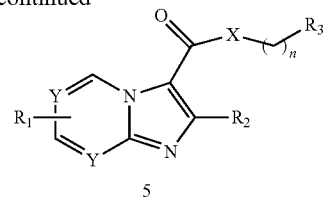

Where:
Y = CH or N;
Z = Br, Cl, I;
X = O, NH;
n = 0, 1 - 4;
R1 = alkyl, alkoxy, halogen, etc.
R2 = alkyl, aryl, $CF_3$, etc.
R3 = aryl, heteroaryl, heterocycle, etc.

Reagents:
(a) N-Z-succinimide, DMSO, room temperature, 4 hours, where Z=Bromo, Chloro, or Iodo;
(b) 1,2-dimethoxyethane, reflux, 48 hours;
(c) 1N LiOH, EtOH, reflux, 36 hours;
(d) oxalyl chloride, $CH_2Cl_2$, DMF (cat.), room temperature, 4 hours;
(e) R—$NH_2$ or R—OH, EDC—HCl, DMAP, $CH_3CN$, 16 hours; when chloride
(f) R—$NH_2$ or R—OH, $Et_3N$, $CH_2Cl_2$, 16 hours.

FIG. 1 shows that ND-8454 may be made from readily available materials using the process described above. The active pharmaceutical ingredient may be obtained at a $300-1000/kg price range on commercial scale. This translates to a remarkably low cost of only $0.03-$0.1/day at a 100 mg daily dose. Therefore, ND-8454 and similar imidazo[1,2-a]pyridine agents are very inexpensive to manufacture and may be made readily accessible to populations in need.

Embodiments of the present disclosure also provide methods for treating or preventing TB infection in a subject using compounds described herein. As used herein, the terms "tuberculosis" and "TB" refer to mycobacterial infection, a common and often deadly infectious disease usually caused by *Mycobacterium tuberculosis*. Tuberculosis usually attacks the lungs (as pulmonary TB), but can also affect the central nervous system, the lymphatic system, the circulatory system, the genitourinary system, the gastrointestinal system, bones, joints, and even the skin. Other mycobacteria such as *Mycobacterium bovis, Mycobacterium africanum, Mycobacterium canetti,* and *Mycobacterium microti* also cause tuberculosis, but these species are less common in humans.

The classic symptoms of tuberculosis are a chronic cough with blood-tinged sputum, fever, night sweats, and weight loss. Infection of other organs causes a wide range of symptoms. In some embodiments, a tuberculosis diagnosis may be made by radiology (commonly chest X-rays), a tuberculin skin test, and blood tests, as well as microscopic examination and microbiological culture of bodily fluids. Tuberculosis treatment is difficult and normally requires long courses of multiple antibiotics, and antibiotic resistance is a growing problem.

Approximately one third of the world's population is infected with *M. tuberculosis*. However, most of these cases will not develop the full-blown disease; asymptomatic, latent infection is most common. About one in ten of these latent infections will eventually progress to active disease, which, if left untreated, kills more than half of its victims. In 2004, mortality and morbidity statistics included 14.6 million chronic active cases, 8.9 million new cases, and 1.6 million deaths, mostly in developing countries. In addition, a rising number of people in the developed world are contracting tuberculosis because of compromised immune systems from immunosuppressive drugs, substance abuse, or AIDS. The distribution of tuberculosis is not uniform worldwide, with about 80% of the population in many Asian and African countries testing positive in tuberculin tests, while only 5-10% of the US population tests positive. It is estimated that the US has 25,000 new cases of tuberculosis each year, 40% of which occur in immigrants from countries where tuberculosis is endemic.

An estimated 75% of active TB cases involve pulmonary TB. Symptoms include chest pain, coughing up blood, a productive, prolonged cough for more than three weeks, fever, chills, night sweats, appetite loss, weight loss, pallor, and often a tendency to fatigue very easily. In the other 25% of active cases, the infection moves from the lungs, causing extrapulmonary tuberculosis. This occurs more commonly in immunosuppressed persons and young children. Extrapulmonary infection sites include the pleura in tuberculosis pleurisy, the central nervous system in meningitis, the lymphatic system in scrofula of the neck, the genitourinary system in urogenital tuberculosis, and bones and joints in Pott's disease of the spine. An especially serious form is disseminated TB, more commonly known as miliary tuberculosis. Although extrapulmonary TB is not contagious, it may co-exist with pulmonary TB, which is contagious.

The primary cause of TB, *Mycobacterium tuberculosis*, is an aerobic, Gram-positive bacterium. In addition, the *M. tuberculosis* complex includes three other TB-causing mycobacteria: *M. bovis, M. africanum* and *M. microti*. *M. africanum* is not widespread, but in parts of Africa it is a significant cause of tuberculosis. *M. bovis* was once a common cause of tuberculosis, but the introduction of milk pasteurization has largely eliminated this as a public health problem in developed countries. *M. microti* is mostly seen in immunodeficient people, although it is possible that the prevalence of this pathogen has been underestimated.

Other known pathogenic mycobacteria include *Mycobacterium leprae, Mycobacterium avium* and *M. kansasii*. The last two are part of the non-tuberculous mycobacteria (NTM) group. Nontuberculous mycobacteria cause neither TB nor leprosy, but they do cause pulmonary diseases resembling TB.

Specific gene polymorphisms in IL12B have been linked to tuberculosis susceptibility. Additionally, patients with diabetes mellitus are at increased risk of contracting tuberculosis, and they have a poorer response to treatment, possibly due to poorer drug absorption. Other conditions that increase risk include IV drug abuse; recent TB infection or a history of inadequately treated TB; chest X-ray suggestive of previous TB, showing fibrotic lesions and nodules; silicosis; prolonged corticosteroid therapy and other immunosuppressive therapy; head and neck cancers; hematologic and reticuloendothelial diseases, such as leukemia and Hodgkin's disease; end-stage kidney disease; intestinal bypass or gastrectomy; chronic malabsorption syndromes; vitamin D deficiency; and low body weight. Furthermore, some drugs, including rheumatoid arthritis drugs that work by blocking tumor necrosis factor-alpha, raise the risk of activating a latent infection due to the importance of this cytokine in the immune defense against TB. In embodiments, a subject having one or more of these risk factors may be a suitable candidate for effective therapies that treat or prevent TB.

As discussed above, compounds in accordance with embodiments of the present disclosure are designed to exhibit anti-TB activity. Methods are provided, in some embodiments, for treating or preventing tuberculosis in a subject. Briefly, the method includes selecting a subject in need of treatment and administering to the subject a therapeutically effective amount of at least one compound having the formula:

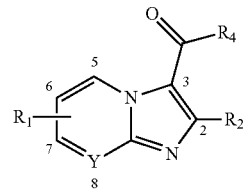

or a pharmaceutically acceptable salt thereof. According to embodiments, $R_1$=alkyl, substituted alkyl, cycloalkyl, functionalized alkyl, cycloheteroalkyl, aryl, substituted aryl, heteroaryl, substituted heteroaryl, or heterocylic, wherein $R_1$ is mono or polysubstituted; $R_2$=alkyl, substituted alkyl, cycloalkyl, functionalized alkyl, cycloheteroalkyl, aryl, substituted aryl, heteroaryl, substituted heteroaryl, or heterocylic, wherein $R_2$ is mono or polysubstituted; $R_3$=H, alkyl, substituted alkyl, cycloalkyl, functionalized alkyl, cycloheteroalkyl, acyl, substituted acyl, haloacyl, aryl, substituted aryl, heteroaryl, substituted heteroaryl, or heterocylic, wherein $R_3$ is mono or polysubstituted, wherein $R_3$ is not a methyl ester, ethyl ester, t-butyl ester, or thiazoline; and Y=CH or N anywhere on positions 5, 6, 7 or 8.

In an embodiment, a further compound may have the formula:

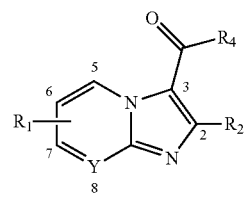

or a pharmaceutically acceptable salt thereof. According to embodiments, $R_1$=alkyl, substituted alkyl, cycloalkyl, functionalized alkyl, cycloheteroalkyl, aryl, substituted aryl, heteroaryl, substituted heteroaryl, or heterocylic, wherein $R_1$ is mono or polysubstituted; $R_2$=alkyl, substituted alkyl, cycloalkyl, functionalized alkyl, cycloheteroalkyl, alkoxy, aryl, substituted aryl, heteroaryl, substituted heteroaryl, wherein $R_2$ is mono or polysubstituted; Y=CH or N anywhere on positions 5, 6, 7 or 8; and $R_4$=$OR_1$, $NHR_1$, $NR_1R_2$, $NHNR_1$, or $NHOR_1$.

In specific, non-limiting examples, the compounds may have the formula:

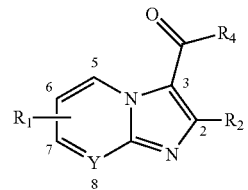

wherein:
  (a) $R_1$=7-$CH_3$, $R_2$=$CH_3$, $R_4$=(3-chloro-5-(trifluoromethyl)pyridin-2-yl)methanamine (ND-9902);

(b) $R_1$=7-$CH_3$, $R_2$=$CH_3$, $R_4$=4-(4-(trifluoromethyl)phenoxy)aniline (ND-9903);

(c) $R_1$=7-$CH_3$, $R_2$=$CH_3$, $R_4$=4-(4-fluorophenoxy)benzylamino (ND-9758);

(d) $R_1$=7-$CH_3$, $R_2$=$CH_3$, $R_4$=(3-ethoxy)benzylamino (ND-9906);

(e) $R_1$=7-$CH_3$, $R_2$=$CH_3$, $R_4$=(3-isopropoxy)benzylamino (ND-9872); or (f) $R_1$=6-$CH_3$, $R_2$=$CH_3$, $R_4$=(4-methylsulfonyl)benzylamino (ND-9965).

In embodiments, when screened in vitro, it was apparent that the imidazo[1,2-a]pyridines had advantages over the other anti-TB heterocycles evaluated previously. For instance, while levels of potency of the ester analogs (notably, benzyl and ethyl) were good in various heterocyclic series (oxazolines, oxazoles, thiazolines, thiazoles and imidazo[1,2-a]pyridines), these esters were metabolically labile. While the corresponding amides were anticipated to be more stable, their anti-TB activity was dramatically decreased, except for the imidazo[1,2-a]pyridine benzyl amides ($NHCH_2Ph$), which were more potent. In addition, the stability of the imidazo[1,2-a]pyridine analogs in rat, dog and human microsomes were vastly improved (>80% remained after a 15 minute incubation). Furthermore, unlike the other heterocyclic scaffolds, the imidazo[1,2-a]pyridines were remarkably metabolically stable in a simulated gastric juice assay (>90% remaining after a 15-minute incubation).

In other embodiments, imidazo[1,2-a]pyridine analogs were generated and optimized using in vitro SAR studies to improve potency, metabolism, organism selectivity and formulation. Briefly, a set of imidazo[1,2-a]pyridine analogs were prepared and subjected to metabolism and organism selectivity profiling. FIG. 2 shows the SAR of particular imidazo[1,2-a]pyridine agents and some trends observed from screening the compounds. (See FIG. 4 for the structures of the compounds referenced in FIG. 2.) The VERO assay is a toxicity assay that measures the viability of African Green Monkey epithelial kidney cells when treated with the compounds being studied. The other assays include three H37Rv TB screens that differ only in the media used: GAS for glycerol-alanine-salts with ferric ammonium citrate, GAST for glycerol-alanine-salts with Tween 80 instead of ferric ammonium citrate, and 7H12, which is a non-glycerol containing medium. The microsomes were derived from male Sprague-Dawley rats and contained drug-metabolizing enzymes, such as cytochrome P450, flavin monooxygenases, and UDP glucuronyl transferases. The simulated gastric juices assay contained pepsins, and was run at pH-1.2.

In embodiments, compounds ND-8448, ND-8451 and ND-8454 were all screened against a panel of diverse organisms which included four Gram-positive strains (*Bacillus subtilis, Staphylococcus aureus*, MRSA *Staphylococcus aureus*, VRE *Enterococcus Faecalis*), two Gram-negative strains (*E. coli, Pseudomonas aeruginosa*), a yeast (*Sporobolomyces salmonicolor*) and fungi (*Candida albicans* and *Penicillium notatum*), as well as five cancer cell lines (Huvec, K-562, HeLa, PC-3 and MCF-7) and the VERO cell line to check for mammalian toxicity. Remarkably, these three compounds were inactive against all of the control organisms studied.

In an embodiment, an evaluation may involve screening of the imidazo[1,2-a]pyridines against H37Rv TB in at least two different assay media, for instance, the GAST (glycerol-alanine-salts with Tween 80) and 7H12 (non-glycerol containing medium), to ensure that potency is not adversely affected by either glycerol or Tween and is not carbon source dependant. Compounds that have MIC's less than 5 µM are then screened in the VERO cellular toxicity and LORA TB recovery assay (an assay designed to simulate the latent TB state). The most impressive compounds that have outstanding potency (MIC<1 µM) and a large therapeutic window (IC50>128 µM in the VERO assay) are then evaluated in rat microsomes and simulated gastric juices.

In an embodiment, compounds ND-8454, ND-8667, and ND-9361 were all screened against a panel of extreme drug-resistant TB strains HRESPOCTh, HREPKOTh, HRESPO, and then cross screened against *M. smegmatis*. As illustrated below in Table 4, all three drugs were effective against the extreme drug-resistant (XDR) strains.

TABLE 4

XDR-TB activity of imidazopyridine agents (MIC90 values in µg/mL)

| Resistance to (µg/mL): | HRESPOCTh | HREPKOTh | HRESPO | *M. smegmatis* |
|---|---|---|---|---|
| ND-8454 | 0.02 | 0.02 | 0.039 | >=5 |
| ND-8667 | 0.01 | 0.0049 | 0.0049 | >=5 |
| ND-9361 | 0.02 | 0.01 | 0.01 | >=5 |

Abbreviations: H = Isoniazid, R = Rifampicin, E = Ethambutol, Z = Pyrazinamide, S = Streptomycin, C = Cycloserine, Th = Ethionamide, K = Kanamycin, P = p-aminosalicylic acid, Rb = Rifabutin, Th = Thioacetazone, O = Ofloxacin.

In another embodiment, compounds ND-8454, ND-9652, ND-9758, ND-9872, ND-9902, ND-9903, and ND-9965 were screened against several non-tubercular mycobacteria (NTM). As illustrated below in Table 5, all seven drugs were effective against *M. avium, M. bovis* BCG and *M. kansasii* and other non-tubercular mycobacterial strains to a lesser extent, indicating that the imidazo[1,2-a]pyridines are selective anti-mycobacterial agents.

TABLE 5

NTM activity of imidazopyridine agents (MIC90 in µM)

|  | *M. chelonae* | *M. marinum* | *M. avium* | *M. kansasii* | *M. bovis* BCG |
|---|---|---|---|---|---|
| ND-8454 | >50 | >50 | 1.32 | 1.32 | 0.33 |
| ND-9652 | >50 | >50 | 12.00 | 12.00 | 2.78 |
| ND-9758 | 6.07 | 5.21 | <0.195 | <0.195 | <0.195 |
| ND-9872 | >50 | >50 | 0.71 | 0.71 | <0.195 |
| ND-9902 | >50 | >50 | 4.42 | 4.42 | 0.75 |
| ND-9903 | >50 | >50 | 0.30 | 0.30 | <0.195 |
| ND-9965 | >50 | >50 | 6.03 | 6.03 | 0.23 |
| INH | >500 | >500 | >500 | 5.82 | <1.953 |
| EMB | >2000 | 965.56 | >2000 | <7.813 | <7.813 |

As discussed above, embodiments provide a method for treating or preventing TB. The method includes selecting a subject in need of treatment and administering to the subject a therapeutically effective amount of at least one compound disclosed herein. As used herein, the term "therapeutically effective amount" includes a quantity of a specified compound (such as one of the imidazo[1,2-a]pyridine compounds disclosed herein, for instance compound ND-8454) required to achieve a desired effect in a subject being treated. For instance, this may be the amount necessary to treat a mycobacterial infection, such as a *Mycobacterium tuberculosis, M. bovis, M. africanum* or *M. microti* infection in a subject, or a dose sufficient to prevent advancement, or to cause regression of a disease (such as TB), or that is capable of relieving symptoms caused by a disease, pulmonary or extrapulmonary symptoms. In some embodiments, a therapeutically effective amount of an imidazo[1,2-a]pyridine compound is a dose that is sufficient to inhibit the progression from latent TB to active TB, or to prevent re-activation of a TB infection.

Various dosage ranges and administration schedules may be adopted for therapeutic treatment of TB in animal and human subjects with the anti-TB agents disclosed herein. In an embodiment, such a therapeutically effective amount of active component may be in the range of about 0.1 to about 100 mg/kg, or more preferably about 0.1 to about 10 mg/kg, of body weight/day. Such dosages may vary depending upon the requirements of the patient, the severity of the disease, the duration of the disease, whether the infection is latent or active, the mycobacterial strain, whether the *mycobacterium* exhibits drug-resistance, or the particular symptoms (for instance, pulmonary or extrapulmonary) of the TB being treated, and the particular compound being used. In some embodiments, the anti-TB agent may be administered in conjunction with one or more other anti-TB agents, such as rifampin, isoniazid, pyrazinamide, ethambutol, streptomycin, ethionamide, kanamycin, cycloserine, thioacetazone, p-aminosalicylic acid, or ciprofloxacin.

In some embodiments, the anti-TB agent (for instance, ND-8454) may be administered systemically, whereas in other embodiments the anti-TB agent may be administered locally. An effective dose of a disclosed anti-TB agent may be administered systemically in a variety of ways. For instance, systemic administration may be by oral administration or by injection, for instance intravenous, intramuscular, or subcutaneous injection. Local (for instance pulmonary) administration may include inhalational administration. By way of example, one method of administration to the lungs of an individual may be by inhalation through the use of a nebulizer or inhaler. For example, the anti-TB agent may be formulated in an aerosol or particulate and drawn into the lungs using a standard nebulizer well known to those skilled in the art.

An effective amount of an anti-TB compound may be administered in a single dose, or in multiple doses, for example daily, or every four, eight, or twelve hours, during a course of treatment. In one embodiment, a therapeutically effective amount of an anti-TB compound may be administered as a single pulse dose, as a bolus dose, or as pulse doses administered over time. In specific, non-limiting examples, pulse doses of an anti-TB compound may be administered during the course of a day, during the course of a week, during the course of a month, or over the course of years.

In other embodiments, the imidazo[1,2-a]pyridine compounds disclosed herein are used to inhibit fungal growth on plant species. In embodiments, the imidazo[1,2-a]pyridine compound may have the formula:

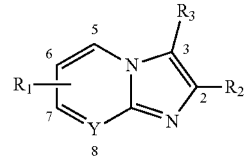

or a pharmaceutically acceptable salt thereof, wherein $R_1$=alkyl, substituted alkyl, cycloalkyl, functionalized alkyl, cycloheteroalkyl, aryl, substituted aryl, heteroaryl, substituted heteroaryl, or heterocylic, wherein $R_1$ is mono or polysubstituted; $R_2$=alkyl, substituted alkyl, cycloalkyl, functionalized alkyl, cycloheteroalkyl, alkoxy, aryl, substituted aryl, heteroaryl, substituted heteroaryl, wherein $R_2$ is mono or polysubstituted; $R_3$=H, alkyl, substituted alkyl, cycloalkyl, functionalized alkyl, cycloheteroalkyl, acyl, substituted acyl, haloacyl, aryl, substituted aryl, heteroaryl, substituted heteroaryl, or heterocylic, wherein $R_2$ is mono or polysubstituted and wherein $R_3$ is not a methyl ester; and Y=CH or N anywhere on positions 5, 6, 7 or 8. Other embodiments are fungicidal compositions comprising at least one imidazo[1,2-a]pyridine compound and a phytologically acceptable carrier. Still other embodiments are antifungal formulations that further include at least one additional compound selected from the group consisting of insecticides, and herbicides.

Other embodiments are methods for controlling a fungal infestation. The methods may include, for instance, the steps of providing at least one imidazo[1,2-a]pyridine compound as described above and applying the compound to a surface having or adjacent to a fungal infection or infestation. In embodiments, the composition may include at least one additional compound selected from the group consisting of: insecticides, fungicides, and herbicides. Also disclosed are methods of controlling a fungal infestation. In embodiments, the methods may include the steps of: providing at least one imidazo[1,2-a]pyridine compound as described herein and applying the compound to a surface having or adjacent to a fungal infection or infestation.

In embodiments, the imidazo[1,2-a]pyridine compounds described herein may have a significant fungicidal effect, particularly in agricultural applications, for instance, for use with agricultural crops and horticultural plants. In various embodiments, the imidazo[1,2-a]pyridine compounds described herein may be used to effectively control a variety of undesirable fungi that infect useful plant crops. In specific, non-limiting examples, antifungal activity has been demonstrated, for example against the following representative fungi species: brown rust of wheat (*Puccinia recondita tritici*—PUCCRT) and *septoria* blotch of wheat (*Septoria tritici*—SEPTTR).

Referring to FIG. 3, exemplary imidazo[1,2-a]pyridine compounds were tested in order to measure their ability to prevent fungal infections. (FIG. 4 illustrates the structures of the compounds referenced in FIG. 3.) In embodiments, each exemplary compound's preventative properties were determined by treating a susceptible test plant with the exemplary imidazo[1,2-a]pyridine compound and then exposing the plant to fungal spores. The antifungal activity of the imidazo[1,2-a]pyridine compounds was determined by determining the extent to which the fungal disease was controlled. The compounds were formulated at rates of 200 ppm in 10 vol. % acetone plus 90 vol. % Triton X water (deionized water 99.99 wt %+0.01 wt % Triton X100), giving a "formulated test compound." Formulated test compounds were applied to plants using a turntable sprayer fitted with two opposing air atomization nozzles that delivered approximately 1500 L/ha of spray volume.

All test plants were inoculated with spores of the fungus (for example, PUCCRT or SEPTTR) the day after treatment with the putative fungicide. Next, the plants were incubated in an environment conducive to disease development. Disease severity was evaluated 7 to 25 days later, depending on the speed of disease development.

In a specific, non-limiting example, wheat plants (variety 'Yuma') were grown from seed in a soil-less peat-based potting mixture (Metromix) until the seedlings had a fully expanded first leaf. Each pot contained 3-8 seedlings. These plants were sprayed until wet with the formulated test compounds. On the following day, the leaves were inoculated with an aqueous spore suspension of *Puccinia recondita tritici* and the plants were kept in high humidity overnight to permit the spores to germinate and to infect the leaf. The plants were then transferred to a greenhouse until disease developed on untreated control plants. These tests were carried out at a level of 200 ppm, see, e.g., FIG. 3.

In another specific, non-limiting example, wheat plants (variety 'Yuma') were grown from seed in a 50% pasteurized soil/50% soil-less mix until the seedlings had a fully expanded first leaf. Each pot contained 3-10 seedlings. These plants were sprayed until wet with the formulated test compound. On the following day, the leaves were inoculated with an aqueous spore suspension of *Septoria tritici* and the plants were kept in high humidity (one day in a dark dew chamber followed by three days in a lighted dew chamber) to permit the spores to germinate and to infect the leaf. The plants were then transferred to a greenhouse until disease developed on untreated control plants. These tests were carried out at a level of 200 ppm, see, e.g., FIG. 3.

In embodiments, disease control was determined by visually estimating the percent disease severity in treated and untreated pots 7 to 24 days after inoculation, depending on speed of disease development. Evaluations were typically made 7 or 8 days after inoculation for PUCCRT and 18 to 22 days after inoculation for SEPTTR. Percent disease control (% DC) was calculated by: % DC=(1−% Disease severity treated/% disease severity untreated)*100.

In various embodiments, the imidazo[1,2-a]pyridine compounds described herein may be applied in the form of a composition comprising one or more imidazo[1,2-a]pyridine compounds with a phytologically-acceptable carrier. The compositions may include, for example, concentrated formulations that are dispersed in water or another liquid for application, or dust or granular formulations that are applied without further treatment. The compositions may be prepared according to procedures which are conventional in the agricultural chemical art.

The dispersions in which the imidazo[1,2-a]pyridine compounds are applied may be, in some examples, aqueous suspensions or emulsions prepared from concentrated formulations of the compounds. Such water-soluble, water suspendable, or emulsifiable formulations are either solids, usually known as wettable powers, or liquids, usually known as emulsifiable concentrates, or aqueous suspensions. In embodiments, any material to which the imidazo[1,2-a]pyridine compounds can be added may be used, provided it yields the desired utility without significantly interfering with the fungicidal activity of the imidazo[1,2-a]pyridine compounds.

In embodiments, wettable powders, which may be compacted to form water dispersible granules, may include an intimate mixture of the active imidazo[1,2-a]pyridine compound, an inert carrier, and one or more surfactants. The concentration of the imidazo[1,2-a]pyridine compound may be, for example, from about 10 percent weight/weight (% w/w) to about 90% % w/w, and may be from about 25% to about 75% w/w in particular examples. In the preparation of exemplary wettable powder compositions, the active ingredients can be compounded with any finely divided solid, such as pyrophyllite, talc, chalk, gypsum, Fuller's earth, bentonite, attapulgite, starch, casein, gluten, montmorillonite clays, diatomaceous earth, purified silicate, or the like. In such examples, the finely divided carrier may be ground or mixed with the toxicant in a volatile organic solvent. Specific, non-limiting examples of effective surfactants, for instance, comprising from about 0.5% to about 10% of the wettable powder, that can be used in combination with the inventive compounds, include sulfonated lignins, naphthalenesulfonates, alkylbenzenesulfonates, alyl sulfates, and non-ionic surfactants such as ethylene oxide adducts of alkyl phenols.

In various embodiments, emulsifiable concentrates of the imidazo[1,2-a]pyridine compounds disclosed herein may comprise a convenient concentration, such as from about 10% to about 50% w/w, in a suitable liquid. Briefly, one exemplary method for creating these emulsions includes the step of dissolving the compound in an inert carrier (for instance, either a water miscible solvent or a mixture of water-immiscible organic solvents and emulsifiers). In specific embodiments, the concentrates may be diluted with water and oil to form spray mixtures in the form of oil-in-water emulsions. Specific, non-limiting examples of organic solvents that may be used include aromatics, especially the high-boiling naphthalenic and olefinic portions of petroleum such as heavy aromatic naphtha and the like. In other embodiments, other organic solvents may be used, such as terpenic solvents, for instance rosin derivatives, aliphatic ketones, such as cyclohexanone, and complex alcohols such as 1-ethoxyethanol.

In some embodiments, emulsifiers may be used, for instance various non-ionic, anionic, cationic, and amphoteric emulsifiers, or a blend of two or more emulsifiers. Specific, non-limiting examples of non-ionic emulsifiers useful in preparing the emulsifiable concentrates include the polyalkylene glycol ethers and condensation products of alkyl and aryl phenols, aliphatic alcohols, aliphatic amines, or fatty acids with ethylene oxide, propylene oxides such as the ethoxylated alkyl phenols, and carboxylic esters solubilised with polyol or polyoxyalkylene. Specific, non-limiting examples of cationic emulsifiers include quaternary ammonium compounds and fatty amine salts. Specific, non-limiting examples of nionic emulsifiers include the oil-soluble salts (e.g., calcium) of alkylaryl sulfonic acids, oil-soluble salts of sulphated polyglycol ethers, and appropriate salts of phosphated polyglycol ether.

Specific, non-limiting examples of organic liquids that may be employed in preparing the emulsifiable concentrates include aromatic liquids such as xylene, propyl benzene fractions or mixed naphtlalene fractions, mineral oils, substituted aromatic organic liquids such as dioctyl phthalate, kerosene, and dialkyl amides of various fatty acids; particularly the dimethyl amides of fatty glycols and glycol derivatives such as the n-butyl ether, ethyl ether, or methyl ether of triethylene glycol. In some embodiments, mixtures of two or more organic liquids may be employed in the preparation of the emulsifiable concentrate. Specific, non-limiting examples organic liquids that may be used include xylene and propyl benzene fractions. In specific, non-limiting examples, surface active dispersing agents may be used in liquid compositions in the amount of from about 0.1 weight % (wt. %) to about 20 (wt. %) of the combined weight of the dispersing agent and active compound. In embodiments, the imidazo[1,2-a]pyridine compositions may also contain other compatible additives, for example, plant growth regulators and other biologically active compounds used in agriculture.

According to various embodiments, aqueous suspensions may include suspensions of water-insoluble imidazo[1,2-a]pyridine compounds, dispersed in an aqueous vehicle at a concentration in the range of from about 5% to about 50% w/w. In one specific, non-limiting example, a suspension may be prepared by finely grinding the compound and vigorously mixing it into a vehicle including water and surfactants as discussed above. In embodiments, inert ingredients, such as inorganic salts and synthetic or natural gums, may also be added, for instance to increase the density and viscosity of the aqueous vehicle. In particular embodiments, it is effective to grind and mix the compound at the same time by preparing the aqueous mixture and homogenizing it in an implement such as a sand mill, ball mill, or piston-type homogenizer.

In other embodiments, the imidazo[1,2-a]pyridine compounds may be applied as granular compositions, which are particularly useful when applying the composition to the soil. Specific, non-limiting examples of granular compositions may include from about 0.5% w/w of to about 10% w/w of the compound dispersed in an inert carrier that includes entirely or in large part a coarsely divided attapulgite, bentonite, diatomite, clay, or a similar inexpensive substance. Such compositions may be prepared, for example, by dissolving the compound in a suitable solvent and applying it to a granular carrier which has been preformed to the appropriate particle size, for instance, in the range of from about 0.5 to about 3 mm. In various embodiments, such compositions may also be formulated by making a dough or paste of the carrier and compound, and crushing, and drying to obtain the desired granular particle.

In other embodiments, dusts that include the imidazo[1,2-a]pyridine compounds may be prepared by intimately mixing the compound in powdered form with a suitable dusty agricultural carrier such as, for example, kaolin clay, ground volcanic rock, and the like. In specific, non-limiting examples, such dusts may include from about 1% w/w to about 10% w/w of the compound.

According to various embodiments, the imidazo[1,2-a]pyridine compositions may contain adjuvant surfactants to enhance properties such as deposition, wetting, and penetration of the compositions onto the target crop and organism. In embodiments, these adjuvant surfactants may be employed as a component of the formulation or as part of a tank mix. The amount of adjuvant surfactant may vary, in specific, non-limiting examples, from about 0.01 percent to about 1.0% volume/volume based on a spray-volume of water. In particular embodiments, the amount of adjuvant surfactant may be, for example, from about 0.05% to about 0.5% volume/volume. Specific, non-limiting examples of adjuvant surfactants include ethoxylated nonyl phenols, ethoxylated synthetic or natural alcohols, salts of the esters of sulphosuccinic acids, ethoxylated organosilicones, ethoxylated fatty amines, and blends of surfactants with mineral or vegetable oils.

In embodiments, the imidazo[1,2-a]pyridine compositions may include combinations that include, for instance, at least 1% of one or more imidazo[1,2-a]pyridine compounds with another agriculturally active ingredient (AI). Such additional AI may include, for example, fungicides, insecticides, nematocides, miticides, arthropodicides, bactericides, herbicidal, or combinations thereof that are compatible with the imidazo[1,2-a]pyridine compounds in the medium selected for application. Accordingly, in such embodiments, the other AI is employed as a supplemental AI for the same or for a different use with plants than the inventive compounds. In specific, non-limiting examples, the compounds in combination may generally be present in a ratio of from about 1:10 to about 100:1.

Other embodiments are methods for the control or prevention of fungal infection. These methods may include applying the active imidazo[1,2-a]pyridine compounds to the locus of the fungus, or to a locus in which the infestation is to be prevented (for example applying it to a cereal or grape plant). In embodiments, the imidazo[1,2-a]pyridine compounds may be used for treatment of various plants at fungicidal levels while exhibiting low phytotoxicity. In addition, in embodiments, the compounds may be used as a protectant or eradicant. In embodiments, such compounds may be applied by any of a variety of known techniques, either as the compounds or as compositions including the compounds. For example, the compounds may be applied to the roots, seeds, or foliage of plants for the control of various fungi without damaging the commercial value of the plants. In embodiments, the materials are applied in the form of any of the generally used formulation types, for example, as solutions, dusts, wettable powders, flowable concentrates, or emulsifiable concentrates.

As described above, in embodiments, the imidazo[1,2-a]pyridine compounds may have significant fungicidal effects, particularly for agricultural use. In particular embodiments, the imidazo[1,2-a]pyridine compounds are effective for use with agricultural crops and horticultural plants, or for the prevention or treatment of fungal growth in other materials, such as wood, paint, leather, or carpet backing.

In particular embodiments, the imidazo[1,2-a]pyridine compounds may effectively control a variety of undesirable fungi which infect useful plant crops. In specific embodiments, the imidazo[1,2-a]pyridine compounds may have activity against a variety of fungi, including, for example, the following representative fungi species: downy mildew of grape (*Plasmopara viticola*—PLASVI), late blight of tomato (*Phytophthora infestants*—PHYTIN), apple scab (*Venturia inaequalis*—VENTIN), brown rust of wheat (*Puccinia recondita tritici*—PUCCRT), stripe rust of wheat (*Puccinia striiformis*—PUCCST), rice blast (*Pyricularia oryzae*—PYRIOR), *Cercospora* leaf spot of beet (*Cercospora beticola*—CERCBE), powdery mildew of wheat (*Erysiphe graminis*—ERYSGT), leaf blotch of wheat (*Septoria tritici*—SEPTTR), sheath blight of rice (*Rhizoctonia solani*—RHIZSO), eyespot of wheat (*Pseudocercosporella herpotrichoides*—PSDCHE), brown rot of peach (*Monilinia fructicola*—MONIFC), and glume blotch of wheat (*Leptosphaeria nodorum*—LEPTNO).

In embodiments, the amount of imidazo[1,2-a]pyridine compound applied for a particular use may depend not only on the specific active material being applied, but also on the particular action desired, the fungal species to be controlled, and the stage of growth thereof, as well as the part of the plant or other product to be contacted with the active ingredient.

Although certain embodiments have been illustrated and described herein, it will be appreciated by those of ordinary skill in the art that a wide variety of alternate and/or equivalent embodiments or implementations calculated to achieve the same purposes may be substituted for the embodiments shown and described without departing from the scope. Those with skill in the art will readily appreciate that embodiments may be implemented in a very wide variety of ways. This application is intended to cover any adaptations or variations of the embodiments discussed herein. Therefore, it is manifestly intended that embodiments be limited only by the claims and the equivalents thereof.

What is claimed is:

1. A compound, having the following formula or a pharmaceutically acceptable salt thereof:

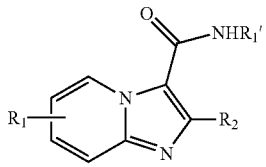

wherein $R_1'$ is independently alkyl, substituted alkyl, cycloalkyl, cycloheteroalkyl, aryl, substituted aryl, heteroaryl, substituted heteroaryl, or heterocycle, or halogen; and wherein $R_1$ is halogen or methyl, and $R_2$ is methyl or ethyl.

2. The compound of claim 1, wherein $R_1$ is halogen.

3. The compound of claim 1, wherein $R_1$ is methyl.

4. The compound of claim 1, wherein $R_2$ is ethyl.

5. The compound of claim 1, wherein $R_1$ is halogen or methyl, and $R_2$ is methyl.

6. The compound of claim 1, which has one of the following formulas or a pharmaceutically acceptable salt thereof:

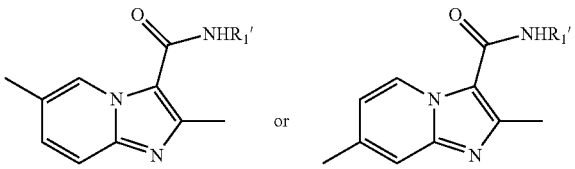

wherein $R_1'$ is substituted alkyl.

7. The compound of claim 6, wherein the structure:

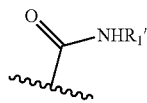

is:

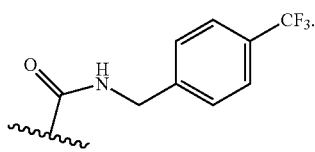

8. The compound of claim 6, wherein $R_1'$ is $C_1$-$C_{12}$ alkyl substituted with 1-4 optionally substituted substituents selected from the group consisting of heterocycle, heteroaryl, cycloalkyl, cycloalkenyl, and aryl.

9. The compound of claim 8, wherein $R_1'$ is methyl substituted with 1-4 optionally substituted substituents selected from the group consisting of heterocycle, heteroaryl, and aryl.

10. The compound of claim 8, wherein $R_1'$ is methyl, and the heterocycle, heteroaryl, and aryl are substituted with 1-4 substituents selected from the group consisting of halogen and $Q_{15}$;

wherein said $Q_{15}$ is independently selected from the group consisting of H, alkyl, cycloalkyl, heteroaryl, phenyl, or naphthyl, each optionally substituted with 1-4 substituents independently selected from the group consisting of F, Cl, Br, I, $-OQ_{16}$, $-SQ_{16}$, $-S(O)_2Q_{16}$, $-S(O)Q_{16}$, $-OS(O)_2Q_{16}$, $-C(=NQ_{16})Q_{16}$, $-S(O)_2-N=S(O)(Q_{16})_2$, $-S(O)_2-N=S(Q_{16})_2$, $-SC(O)Q_{16}$, $-NQ_{16}Q_{16}$, $-C(O)Q_{16}$, $-C(S)Q_{16}$, $-C(O)OQ_{16}$, $-OC(O)Q_{16}$, $-C(S)NQ_{16}Q_{16}$, $-C(O)C(Q_{16})_2OC(O)Q_{16}$, $-CN$, $-NQ_{16}C(O)Q_{16}$, $-NQ_{16}C(S)Q_{16}$, $-NQ_{16}C(O)NQ_{16}Q_{16}$, $-NQ_{16}C(S)NQ_{16}Q_{16}$, $-S(O)_2NQ_{16}Q_{16}$, $-NQ_{16}S(O)_2Q_{16}$, $-NQ_{16}S(O)Q_{16}$, $-NQ_{16}SQ_{16}$, $-NO_2$, and $-SNQ_{16}Q_{16}$; wherein the $Q_{15}$ alkyl, and cycloalkyl may be further optionally substituted with =O or =S; wherein $Q_{16}$ is independently selected from the group consisting of H, alkyl, and cycloalkyl; and wherein the $Q_{16}$ alkyl and cycloalkyl may optionally include 1-3 halogens.

11. The compound of claim 8, wherein $R_1'$ is methyl, and the heterocycle, heteroaryl, and aryl are substituted with 1-4 substituents selected from the group consisting of halogen and $Q_{15}$, said $Q_{15}$ being selected from the group consisting of alkyl, cycloalkyl, heteroaryl, phenyl, and napthyl and optionally substituted with 1-4 substituents independently selected from the group consisting of F, Cl, Br, and I.

12. The compound of claim 8, wherein $R_1'$ is methyl substituted with aryl or benzofuran, the aryl being substituted with trifluoromethyl.

13. A pharmaceutical composition comprising the compound of claim 1 and a pharmaceutically acceptable carrier.

14. A method of treating tuberculosis in a subject, the method comprising selecting a subject in need of treatment and administering to the subject a therapeutically effective amount of the compound of claim 1, thereby treating the tuberculosis in the subject.

15. The method of claim 14, wherein the subject is human.

16. The method of claim 14, wherein the tuberculosis is an active or latent infection of *M. tuberculosis*.

17. The method of claim 14, wherein administration comprises oral, inhalational, parenteral, intravenous, intramuscular, or subcutaneous administration.

18. The method of claim 14, further comprising the administration of one or more additional agents effective in treating tuberculosis.

19. The method of claim 18, wherein the one or more additional agents is isoniazid or rifampin.

* * * * *